(12) United States Patent
Ben Shalom

(10) Patent No.: US 7,988,614 B2
(45) Date of Patent: Aug. 2, 2011

(54) ORGAN ASSIST SYSTEM AND METHOD

(76) Inventor: Zvi Ben Shalom, Bat Hadar (IL)

( * ) Notice: Subject to any disclaimer, the term of this patent is extended or adjusted under 35 U.S.C. 154(b) by 318 days.

(21) Appl. No.: 11/996,194

(22) PCT Filed: Jul. 19, 2006

(86) PCT No.: PCT/IL2006/000838
§ 371 (c)(1),
(2), (4) Date: Jan. 18, 2008

(87) PCT Pub. No.: WO2007/010535
PCT Pub. Date: Jan. 25, 2007

(65) Prior Publication Data
US 2008/0214888 A1    Sep. 4, 2008

(51) Int. Cl.
*A61N 1/372* (2006.01)
(52) U.S. Cl. .................................. 600/17; 623/3.21
(58) Field of Classification Search .............. 600/16, 600/17; 623/3.21
See application file for complete search history.

(56) References Cited

U.S. PATENT DOCUMENTS

| | | | |
|---|---|---|---|
| 2,826,193 A * | 3/1958 | Vineberg | 601/153 |
| 4,192,293 A | 3/1980 | Asrican | |
| 5,437,610 A | 8/1995 | Cariapa et al. | |
| 5,672,148 A | 9/1997 | Maunier | |
| 5,713,954 A | 2/1998 | Rosenberg et al. | |
| 6,206,820 B1 | 3/2001 | Kazi | |
| 6,251,061 B1 | 6/2001 | Hastings et al. | |
| 6,406,422 B1 | 6/2002 | Landesberg | |
| 6,508,756 B1 | 1/2003 | Kung et al. | |
| 6,589,194 B1 | 7/2003 | Calderon et al. | |
| 6,602,182 B1 * | 8/2003 | Milbocker | 600/16 |
| 2004/0092790 A1 * | 5/2004 | Yadav et al. | 600/16 |

FOREIGN PATENT DOCUMENTS

| | | |
|---|---|---|
| WO | 98/55165 | 6/1997 |
| WO | 2005/002645 | 6/2004 |

* cited by examiner

*Primary Examiner* — Niketa I Patel
*Assistant Examiner* — Alyssa M Alter
(74) *Attorney, Agent, or Firm* — Renner, Otto, Boisselle & Sklar, LLP

(57) ABSTRACT

An organ assist system having a closed fluid system having a ring-shaped prosthetic contactively surrounding at least a portion of a body part, including bladders adapted for selectable dilation and contraction in response to varying fluid pressure therewithin, a fluid pump, and apparatus for pressurizing the bladders; and a control unit for controlling operation of at least the fluid pump; pressure sensors within the fluid system; a power source, and shut off valves. The pressurization apparatus includes pressure cells arranged in an array, each pressure cell having a shut-off valve at its inlet, and a shut-off valve at its outlet, the shut-off valves being controlled by the control unit such that the pressurization apparatus is operable to provide a range of pressurizations to the bladders of the prosthetic for applying a controlled variable pressurizing effect to the body part thereby.

27 Claims, 9 Drawing Sheets

ORGAN ASSIST SYSTEM AND METHOD

FIELD OF THE INVENTION

The present invention relates generally to the application of pressure to a body organ or limb so as to assist the organ or limb in performing its intended function.

DEFINITION

In the present specification and claims, the terms "organ" and "body part" are used interchangeably, and refer generally to any portion of a mammalian body that may benefit from a blood flow assist system, including, but not limited to, the heart and thighs of a human.

BACKGROUND OF THE INVENTION

In recent years, there have been many developments in the field of cardiac assistance, with a plethora of devices and systems for aiding the pumping of a dysfunctional heart. One common approach is to use a pacemaker that provides an electrical pulse that causes the heart to dilate. Another approach is to perform a heart transplant, replacing the heart with a donor heart. A further approach is to use an artificial heart. Artificial hearts are particularly useful as short term, bridging solutions until appropriate donor hearts are available.

A third approach is to provide a heart assist device, essentially a prosthetic that is wrapped around the heart, or a part thereof, such as to the left ventricle, for example. Contraction of the prosthetic provides a squeezing force on the heart helping it to pump.

A variety of mechanical cardiac devices have been developed, including pumps that serve as ventricular assist devices and full artificial hearts. Each device performs differently and is appropriate for a different specific function.

In 1969, the world's first total artificial heart implant was performed by Dr. Denton A. Cooley. The device, developed by Dr. Domingo Liotta, was implanted in a 47-year-old patient with severe heart failure, and supported the patient for nearly three days, until a donor heart was found allowing transplantation. The Liotta total artificial heart was an air-driven (pneumatic), double-ventricle pump. Wada-Cutter hingeless valves controlled the flow of blood through the inflow and outflow areas of the pump. The two pump chambers (the "ventricles"), the cuff-shaped inflow tracts (the "atria"), and the outflow tracts were lined with a special fabric that promoted the formation of a smooth cellular surface. The flexible inflow and outflow tracts were made of Dacron fabric, and the pump chambers were made of Dacron fabric and Silastic plastic. The pumps were connected to the external power unit with Silastic tubing covered by Dacron fabric. The console, also a major engineering accomplishment at the time, was about the size of a large household washing machine. Two pneumatic power units generated the pumping and vacuum actions needed to move blood through the artificial heart. The complex control panel included numerous switches and knobs used to adjust pumping rate and pumping pressure.

In July 1981, Dr. Cooley again implanted a total artificial heart. Developed by Dr. Tetsuzo Akutsu at the Texas Heart Institute, the Akutsu III total artificial heart was implanted in a 36-year-old man, keeping him alive for 55 hours, until a donor heart was found for transplantation. The Akutsu III total artificial heart contained two air-powered, double-chambered pumps. The pumping chambers were made of a smooth material called Avcothane, which could be molded in one piece. The inflow and outflow ports contained Bjork-Shiley disc valves. The prosthetic ventricles were attached to the remnants of the natural heart's atria and to the great vessels by flexible inflow and outflow conduits with detachable quick-connectors. The pumps were connected with Dacron velour-covered tubing to an external control console. The control console had three basic systems: a pneumatic (air-driven) drive system, an electrical monitoring/control system, and an electrical power system. The pneumatic drive system provided both pressure and vacuum to each ventricle. Under normal use, the console was connected to wall pressure and vacuum sources. During patient transport, or in the event of in-house power failure, the system automatically switched to on-board compressed air tanks. Monitoring of heart rate and systolic duration were the primary functions of the electrical monitoring/control system. The monitoring/control system provided a digital readout of driveline pressure and vacuum supplied, as well as the status of standard and emergency power supplies. The electrical power system had two independent sources of power: standard AC/DC power and a back-up battery in case of power failure.

The Jarvik-7 total artificial heart, designed by Dr. Robert Jarvik is probably the best known of the artificial heart devices. It is designed to function like the natural heart. It was first implanted in a patient named Barney Clark in 1982, who survived for 112 days. By the late 1980s, surgeons had used the Jarvik-7 as a bridge to transplantation in more than 70 patients. Subsequently, the Jarvik-7 was called the Symbion total artificial heart. Today, it is known as the CardioWest total artificial heart and is still in use as a bridge to transplantation.

The Jarvik-7 has two pumps, much like the heart's ventricles. Each sphere-shaped polyurethane "ventricle" has a disk-shaped mechanism that pushes the blood from the inlet valve to the outlet valve. The ventricles are pneumatically (air) powered. Air is pulsed through the ventricular air chambers at rates of 40 to 120 beats per minute. The artificial heart is attached to the heart's natural atria by cuffs made of Dacron felt. The drivelines out of the ventricular air chambers are made of reinforced polyurethane tubing. Where they exit the skin, the lines are covered with velour-covered Silastic which ensures stability and encourages tissue growth even with movement by the patient. The air-driven, external power system powers the pump through drivelines that enter the heart through the patient's left side. The large console on wheels is as large and as heavy as a household refrigerator. It is normally connected to sources of compressed air, vacuum, and electricity. The system is backed up by a rechargeable battery in case of power failure and includes on-board compressed air tanks (modified scuba type) for use during patient transport. Controls in the console allow the doctor to control pump rate, pumping pressure, and other essential functions.

The AbioCor™ implantable replacement heart represents the culmination of 30 years of research, development, and testing conducted by ABIOMED, Inc. and its collaborators, with the support of the National Heart, Lung and Blood Institute. It was the first completely self-contained total artificial heart and is designed to sustain the body's circulatory system and to extend the lives of patients who would otherwise die of heart failure. Unlike other systems described hereinabove, it is totally implanted within the body, and patients are not tethered to a large, air-pumping console nor do they have wires or tubes piercing their skin. The AbioCor is intended for use in end-stage heart failure patients whose hearts have irreversible left and right ventricular failure and for whom surgery or medical therapy is inadequate.

The AbioCor consists of a thoracic unit, an internal rechargeable battery, an electronics package and external console. The thoracic unit (the pump) weighs around a kilogram and consists of the artificial ventricles, which contain their corresponding valves, and a motor-driven hydraulic pumping system. The hydraulic pumping system uses pressure to shuttle blood from side to side, from the artificial right ventricle to the lungs or from the artificial left ventricle to the rest of the body. To create this pressure, the pump's motor rotates at 4000 to 8000 revolutions per minute. The internal rechargeable battery is an emergency battery that is continually charged by the external power source. The internal battery can provide up to 20 minutes of operation while disconnected from the main battery pack. The electronics package is implanted in the patient's abdominal area and monitors and controls the pumping speed of the artificial heart. The AbioCor is normally powered by an external console or battery packs. The internal battery powers the pump only when the external power supply is disconnected. Power to the AbioCor is achieved with an energy-transfer device called a transcutaneous energy transmission (TET) system. The TET system consists of internal and external coils that are used to transmit power across the skin. Because tubes or wires do not pierce the skin, the chances of developing an infection are decreased. External battery packs can power the AbioCor for 4 hours.

The ABIOMED BVS-5000 is currently in use worldwide for temporary left, right, or biventricular (both ventricles) support in patients with potentially reversible heart failure. The BVS-5000 underwent preclinical studies at the Texas Heart Institute (THI) from 1986 to 1988 and was introduced for use in patients at THI in 1988. It was the first heart assist device approved by the U.S. Food and Drug Administration for the support of post-cardiotomy patients (those who have developed heart failure as a result of heart surgery). Since that time, hundreds of patients have been sustained by the BVS-5000. In addition to post-cardiotomy support, the BVS-5000 may also be used for donor heart dysfunction or donor heart failure after heart transplantation, right-sided heart failure after placement of a left ventricular assist device, after acute heart attack or acute heart disorders, such as viral myocarditis, after trauma to the heart, after disease of the heart muscle (cardiomyopathy).

In patients whose hearts have not recovered after temporary support, the BVS-5000 may be used as a bridge to another device or as a bridge to heart transplantation. The air-driven blood pump is placed outside the body (extra corporeally). A unique feature of the BVS-5000 system is its dual-chamber design, which is similar to the natural heart, and provides support for either the left or right ventricle, or both. The pump houses two polyurethane chambers: an atrial chamber that fills with blood through gravitational force and a ventricular chamber that pumps blood by air-driven power. The atrial chamber is vented outside the patient. The ventricular chamber is connected to the power console by a 0.25-inch pneumatic (air) line. Two trileaflet valves separate the atrial and ventricular chambers. The pump can produce blood flow of up to 5 liters per minute. Cannulas of various designs (for blood drainage and return) are available to accommodate different patient anatomy. The BVS-5000 console can support one or two blood pumps. It is fully automatic and compensates for changes both in preload and after load. The left and right sides are triggered independently of each other. A backup battery provides 1 hour of support, and an alarm sounds when only 10 minutes of power remain. A foot pump can also serve as a backup power source. By using the console to limit blood flow; patients can be slowly weaned from support.

A related device, the Abiomed AB5000 Circulatory Support System is a short-term mechanical circulatory support system that can provide left, right, or biventricular support for patients whose hearts have failed but have the potential for recovery. The AB5000 can be used to support the heart, giving it time to rest—and potentially recover native heart function. The device can also be used as a bridge to definitive therapy.

Since January 1986, when Dr. O. H. Frazier of the Texas Heart Institute initiated clinical trials thereof, the Thoratec HeartMate®IP LVAS is in use worldwide as a bridge to heart transplantation. It provides physical rehabilitation and greatly improves the clinical status of bridge-to-transplant patients. When patients are supported by the HeartMate for more than 30 days, the outcome of transplantation improves. The pneumatic (air-driven) LVAS pump is a titanium alloy pump that weighs 570 grams and consists of a blood chamber, an air chamber, a driveline, and inflow and outflow conduits. Each conduit is a titanium cage that contains a 25-mm porcine (pig) valve within a woven Dacron-fabric graft. A flexible polyurethane diaphragm separates the blood chamber and the air chamber. Textured surfaces within the blood chamber promote the development of a cellular lining, which helps prevent blood clots and infection. With a stroke volume of 83 milliliters and a maximum pumping rate of 140 beats per minute, the IP LVAS can provide flow rates of up to 12 liters per minute. The HeartMate console powers and controls the implanted IP LVAS blood pump. A 6-foot cable joins the blood pump to the drive console. Another 6-foot long tubing connects from the pump to the console to push air into the pump chamber. A front panel display gives a continuous readout of the pump rate, stroke volume, and total blood flow. The system can operate in three modes: automatic mode, fixed-rate mode, and external (synchronous) mode. The drive console is easy to operate and can be transported on a wheeled cart, allowing patients to move about the hospital.

The Thoratec Heartmate® XVE LVAS was developed and tested by Thermo Cardiosystems, Inc. and the Texas Heart Institute. In 1991, the system was implanted in a patient who was subsequently supported for 505 days and was able to leave the hospital while being supported by this device, paving the way for other patients to routinely wait at home for their transplants. Because the system is relatively easy to use, patients and their families can maintain it outside the hospital setting. Patients can live at home, return to work, and resume a more normal lifestyle while awaiting a suitable donor heart. Recently, the (FDA) approved the HeartMate XVE LVAS as permanent support for end-stage heart failure patients not eligible for heart transplants. The titanium blood pump thereof consists of a blood chamber, a motor chamber, a driveline, and inflow and outflow conduits. The pump weighs a mere 1150 grams. Each conduit contains a 25-mm porcine (pig) valve within a woven Dacron-fabric graft. A polyurethane diaphragm separates the blood chamber and the motor chamber. Textured surfaces within the blood chamber promote the development of a cellular lining, which help prevent blood clots and infection. The XVE LVAS has a maximum stroke volume of 83 milliliters and can be operated at up to 120 beats per minute, resulting in flow rates of up to 10 liters per minute.

The XVE LVAS's external equipment includes a system controller, a power base unit, and a 20-foot power cable, as well as batteries and other accessories. The system controller continuously monitors and controls the implanted motor and shows information regarding alarm conditions. The power base unit serves as a battery charger and as an interface between the system monitor and the implanted pump. The 20-foot power cable allows the system to be operated by AC power. Alternatively, patients can wear a portable battery pack around their waist, which permits the system to be operated tether-free for up to 8 hours.

A further development of the XVE LVAS, the Thoratec HeartMate® II LVAS was developed and tested by Thoratec Corporation, Inc., and the Texas Heart Institute (THI). The HeartMate II is being evaluated initially for use as a bridge to transplantation. Eventually, it is hoped that the HeartMate II can be used for destination therapy—as permanent support for end-stage heart failure patients who are not eligible for heart transplantation.

The HeartMate II is a high-speed, axial flow, rotary blood pump. As an axial flow device, the HeartMate II produces no pulsatile action. Weighing 12 ounces (about 375 grams) and measuring about 1.5 inches (4 cm) in diameter and 2.5 inches (6 cm) long, it is significantly smaller than other currently approved devices. As such, it may be suitable for a wider range of patients, including small adults and children. The internal pump surfaces are fabricated from smooth, polished titanium. Within the pump is a rotor that contains a magnet. The rotor assembly is rotated by the electromotive force generated by the motor. The rotor propels the blood from the inflow cannula out to the natural circulation. The pump speed can vary from 6,000 rpm to 15,000 rpm, providing blood flow of up to 10 liters per minute. The pump can run in two operating modes: fixed speed and auto-speed. In fixed-speed mode, the device operates at a constant speed, which can be adjusted via the system monitor. In the auto-speed mode, the pump speed varies in response to different levels of patient or cardiac activity. The HM II LVAS's external equipment includes a system driver, a power base unit, and a 20-foot power cable, as well as batteries and other accessories. The system driver continuously monitors and controls the implanted motor and shows information regarding alarm conditions. The power base unit serves as a battery charger and an interface between the system monitor and the implanted pump. The 20-foot power cable allows the system to be operated by AC power. Patients can wear a portable battery pack around their waist, which permits the system to be operated tether-free for three hours.

The Thoratec Ventricular Assist Device (VAD) can be used to support patients with acute and chronic heart failure. Doctors have gained approximately 20 years of experience with this system at numerous medical centers around the world. One or two Thoratec VADs can be used to provide left, right, or biventricular support. The blood pump is positioned extra corporeally and is connected to tubes (cannulas) inserted into the heart. The pump has a rigid plastic case that contains a flexible pumping sac. Blood is ejected from the pump when the pumping sac is compressed by air from the external control console. Within the inflow and outflow conduits, mechanical valves control the direction of blood flow. The Thoratec VAD has a stroke volume of 65 milliliters. It can be operated at up to 100 beats per minute, resulting in blood flow rates of up to 7 liters per minute.

The Thoratec console has control modules and internal compressors that provide pressure and vacuum conditions to the pump. The drive console delivers air to the blood pump in a pulse-like fashion, causing blood to be ejected into the aorta and/or pulmonary artery. The drive console may be set to three different modes of operation: (i) an asynchronous mode where pumping occurs at a preset rate, (ii) a synchronous mode where pumping is synchronized with the patient's heart rate and (iii) a volume mode where pumping is adjusted according to the left ventricular filling volume. The console continuously displays the ejection pressure, percent ejection time, pump rate, pump flow, and vacuum pressure. Because of the external placement of the pump(s), patient mobility is limited with this system.

Jarvik Heart, Inc. and the Texas Heart Institute began developing the Jarvik 2000 FlowMaker® in 1988. About the size of a "C" battery, the device is a valve-less, electrically powered axial flow pump that fits directly into the left ventricle and continuously pushes oxygen-rich blood throughout the body. To date, patients have been sustained for more than 400 days with this device. The Jarvik 2000 FlowMaker is an axial flow blood pump that uses electrical power to rotate a vaned impeller—the only moving part. The device is 2.5 cm wide, 5.5 cm long, and weighs 85 grams. The impeller is a neodymium-iron-boron magnet, which is housed inside a welded titanium shell. The impeller is supported by ceramic bearings. A small cable, which exits the body through the abdominal walls delivers power to the impeller. All of the blood-contacting surfaces are made of highly polished titanium. The normal operating range for the control system is 8,000 to 12,000 revolutions per minute, which will generate an average pump flow rate of 5 liters per minute. The pump speed is controlled by an analog system controller. The pump speed can be manually adjusted from 8000 to 12000 rpm in increments of 1000. The control unit monitors the pump function and the remaining power in the batteries. Audible and visual alerts notify the user of any problems.

The Levitronix CentriMag Short-term LVAS comprises a single-use centrifugal pump, a motor, and a primary drive console. Compared to other devices, the Levitronix LVAS is unique in that it is designed to operate without mechanical bearings or seals. This is possible because the motor magnetically levitates the impeller, achieving rotation with no friction or wear.

In the United States, the Levitronix CentriMag LVAS is still under investigation for use as a short-term device that would provide circulatory support of up to 14 days for patients with post-cardiotomy cardiogenic shock, i.e. those who have developed heart failure as a result of heart surgery.

The Levitronix CentriMag is an extra-corporeal, continuous-flow, centrifugal-type rotary blood pump. The pump housing and rotor are made of medical-grade polycarbonate, designed for single-use. The only moving component within the pump is the impeller, which is magnetically levitated and rotated in a contact-free manner. The centrifugal pump design permits rotation of the impeller at lower speeds, while still achieving desired flow rates. The pump can rotate at speeds of 1500 rpm to 5500 rpm and can provide flow rates of up to 9.9 liters per minute.

The Levitronix pump causes very little damage to the blood because it does not contain any bearings or seals—components that are known to cause hemolysis and promote thrombus formation. In addition, the pump does not contain any flexing sacs, diaphragms, or valves, minimizing the risk of component failure and device-related adverse effects.

The TandemHeart Percutaneous Ventricular Assist Device (pVAD) differs from other assist devices in that it can be inserted either by cardiovascular surgeons in the operating room or by cardiologists in the cardiac catheterization laboratory. The TandemHeart has been used in post-cardiotomy cardiogenic shock patients, and as a bridge to a definitive therapy. The TandemHeart pVAD provides short-term support from a few hours up to 14 days, giving the heart time to strengthen and potentially regain native function.

The TandemHeart pVAD is an extra-corporeal, continuous-flow centrifugal assist device. Cannulas are inserted percutaneously through the femoral vein and advanced across the intra-atrial septum into the left atrium. The pump withdraws oxygenated blood from the left atrium, propels it by a magnetically driven, six-bladed impeller through the outflow port, and returns it to one or both femoral arteries via arterial cannulas. The pump weighs 8 ounces and is capable of delivering blood flow up to 3.5 liters per minute. The pump also has a proprietary fluid-infusion system that provides cooling and lubrication to the impeller and enhances thromboresistance. The system provides localized anticoagulation to the blood inside the pump, reducing the need for systemic anticoagulation.

The TandemHeart pVAD is operated by a controller console designed to continuously monitor the system. The console also has extensive back-up and fault-management features.

The Bio-Pump was originally developed for cardiopulmonary bypass, but it can be used for up to about a week of circulatory support beyond the surgical setting. The Bio-Pump has been used both in post-cardiotomy cardiogenic shock patients and as a bridge to transplantation for patients who cannot be weaned from the device. This short-term assist device can be implanted in a broad range of patients, from newborns to adults, and can be used alone or along with another Bio-Pump or other type of assist device if biventricular support is needed.

The Bio-Pump is an extra-corporeal, centrifugal device that can provide support for one or both ventricles. Two disposable models are available: the 80-mL model for adults and a 48-mL model for children. The transparent pump housing is shaped like a cone. The pump consists of an acrylic pump head with inlet and outlet ports placed at right angles to each other. The impeller, which is a stack of parallel cones, is driven by an external motor and power console. Rotation of this impeller at high speeds creates a vortex, which drives blood flow in relation to rotational speed. Blood enters through an inlet at the top of the cone and exits via an outlet at the base. The adult model pump can rotate up to 5000 rpm and can provide flow rates of up to 10 liters per minute.

The Bio-Pump console is relatively small and easy to operate, although it does require continuous supervision by specially trained personnel. When fully charged, the system has an internal battery life of 45 minutes. A battery indicator light displays the charge level. A flow probe inserted in the patient's artery allows for a continuous readout of the blood flow rate. The operator can program the console for use in children or adults by selecting a high or low flow rate. The console features a numeric readout and a bar graph that shows flow rate and revolutions per minute.

The Model-7 ALVAD is a pneumatic abdominal left ventricular assist device (ALVAD) that has been used to support post-cardiotomy patients.

The Model-7 ALVAD is a pneumatic, single-chambered implantable blood pump that was placed in the abdomen and connected to the left ventricle by a Dacron tube. Blood from the left ventricle flows through the tube and fills a polyurethane bladder. When air from the driveline fills the space between the bladder and the titanium pump housing, the blood is pumped through a disc-type valve into the aorta and to the body. Polyester fibers coat all of the blood-contacting surfaces, except the valve discs and the inflow and outflow grafts. The fibers promote the development of a cellular lining, which helps prevent blood clots and infection. The console thereof provides variable settings of pump chamber pressurization, pump chamber filling, and pulse duration. The two modes of operation include EKG-triggered pumping that is synchronized with the resting and pumping phases of the left ventricle, or variable fixed-rate asynchronous pumping. Four fail-safe functions are also available in cases of EKG interruption; mechanical or electrical failure; loss of external pneumatic power or loss of AC line power. The internal power supplies allow for portable operation for up to 50 minutes.

The Impella Recover LD/LP 5.0 Support System has been developed to address the need for ventricular support in patients who develop cardiogenic shock—heart failure after heart surgery—and who have not responded to standard medical therapy. The system is designed to provide immediate support and restore hemodynamic stability for a period of up to 7 days. Used as a bridge to therapy, it allows time for developing a definitive treatment strategy.

The Impella Recover system is a miniaturized impeller pump located within a catheter. The device can provide support for the left side of the heart using either the Recover LD 5.0 that is implanted via direct placement into the left ventricle, or the Recover LP 5.0 LV that is placed percutaneously through the groin and positioned in the left ventricle. The microaxial pump of the Recover LP/LD 5.0 can pump up to 4.5 L/min at a speed of 33,000 rpm. The pump is located at the distal end of a 9 Fr catheter. At its largest outside diameter, which contains the pump housing, the Impella measures 21 Fr. The catheter shaft contains the electrical connections for the pump motor and sensor as well as for a separate tube used for transfer of purged fluid.

Clinical use of the Hemopump in patients began at the Texas Heart Institute in April 1988 as a short-term treatment for cardiogenic shock. Later, the device was evaluated as an alternative to standard cardiopulmonary bypass. Today, the Hemopump is no longer used, but researchers have applied its design to other circulatory assist devices. The innovative design of the Hemopump included a tiny axial flow pump that provided up to 3.5 liters per minute of circulatory support. The first patient treated with the Hemopump was a 61-year-old man with profound heart failure related to donor heart rejection. His life was sustained with the Hemopump for two days, and he was eventually discharged from the hospital. The catheter-mounted, intra-aortic axial flow pump thereof is about the size of the eraser on an ordinary pencil. It was inserted through a small incision in the femoral or external iliac artery, advanced to the aorta, and positioned across the aortic valve. A screw element rotated 17,000 to 25,000 times per minute, drawing blood from the left ventricle and ejecting it into the descending aorta. Power was provided through a percutaneous driveline connected to an external electromechanical console. The console produced flows of up to 3.5 liters per minute and assumed up to 80% of the left ventricle's workload.

Dr. Adrian Kantrowitz introduced the intra-aortic balloon pump (IABP) in the late 1960s as a simple yet effective device to increase coronary perfusion. Because it is easy to insert, the IABP is the most widely used form of mechanical circulatory support. At the Texas Heart Institute, the IABP is now used in more than 450 patients each year. Although the IABP was first used for surgical patients, the pump can now be used along with interventional cardiology procedures and medications. Indications for its use include failure to wean from cardiopulmonary bypass, cardiogenic shock, heart failure, acute heart attack, support during high-risk percutaneous transluminal coronary (balloon) angioplasty, rotoblator procedures, and coronary stent placement.

The IABP is a polyethylene balloon mounted on a catheter, which is generally inserted into the aorta through the femoral artery in the leg. The pump is available in a wide range of sizes (2.5 cc to 50 cc) that will fit patients of any age and size. The balloon is guided into the descending aorta, approximately 2 cm from the left subclavian artery. At the start of diastole, the balloon inflates, augmenting coronary perfusion. At the beginning of systole, the balloon deflates; blood is ejected from the left ventricle, increasing the cardiac output by as much as 40 percent and decreasing the left ventricular stroke work and myocardial oxygen requirements. In this manner, the balloon supports the heart indirectly. The balloon is inflated with helium, an inert gas that is easily absorbed into the bloodstream in case of rupture. Inflation of the balloon can be triggered according to the patient's electrocardiogram, their blood pressure, a pacemaker (if they have one), or by a pre-set internal rate.

The IABP is driven by the balloon pump console. The operating controls are located on a touch pad below the display monitor and can be programmed to produce rates as high as 140 beats per minute. The on-board battery provides power for up to 2 hours. The New CS100 IntelliSync console, with one-button start up, automatically adapts to patients' changing conditions.

Similarly, U.S. Pat. No. 6,406,422 to Landesberg describes a ventricular assist method and apparatus having an expandable intraventricular chamber, essentially a single chambered balloon, for dilating a heart chamber. The device described is not intended to replace the entire function of a failing heart but rather to add additional cardiac input.

PCT/IL2004/000500 (WO 2005/002645) to Ben Shalom et al. describes a hydraulic system and method for supporting a body organ, the system comprising a closed loop liquid-tight tubing fitted with a pressure generator for propelling a liquid through the system, an organ engaging member connected to a pressure chamber via a discharge valve for controlled discharge of liquid into the organ inflatable pressure member. The organ-engaging member includes an inflatable pressure member suited for receiving the organ. There is further provided at least one control valve for selectively controlling liquid flow through the system and a controller for selectively controlling the discharge valve and the at least one control valve. The system may be used as cardiac assist device or for massaging a limb to stimulate blood flow therethrough. The device described has one pulsation chamber, and there is an inherent lack of flexibility therewith in that the system described includes no features for adapting the prosthetic ring to specific diseased hearts.

U.S. Pat. No. 4,192,293 to Asrican, describes a cardiac assist device that operates by cyclically exerting pressure through an implanted inflatable sheath, which surrounds the myocardium. The sheath is rigid and encloses a bladder or plurality of bladders into which a fluid, either in the form of an inert gas or a liquid is pulsed, with a time displacement curve similar or identical to the contraction-distension characteristics exhibited normally by the myocardium during a cardiac cycle. Pulsing is triggered by the EKG R-spike of the patient, which operates a valve. In order to provide adequate fluid volume for the required pressure through the valve, an elastic fluid reservoir is provided. The cyclical pressure is generated by an elastic wall. It is therefore a fixed pressure that is difficult to match to a specific heart, and in practice will only provide a very approximate match. Furthermore, since clearly the appropriate cardiac assistance for an individual varies considerably throughout the day, between sleeping and walking for example, and depends, inter alia, on the amount of exertion and the quality of the air breathed, such a system will only very approximately match actual requirements.

WO 98/55165 to Seare and Woodard, describes a cardiac assist device with independently operable pneumatic or hydraulic chambers. In consequence thereof, the pressure provided at different positions on heart may be varied. The overall shape of the device described may be cup shaped, frustoconical, cylindrical etc. and may be tailored to the shape of the individual heart to provide a tailored solution for a specific diseased heart.

U.S. Pat. No. 5,713,954 to Rosenberg et al. describes a cuff that may be inflated and deflated using hydraulic fluid, which is designed to be placed around the natural heart. The cuff comprises a plurality of tubular segments that are variably fluid filled. Hydraulic pumps and rotating valves are described. Actuators and electronic control are also discussed.

U.S. Pat. No. 6,206,820 to Kazi describes an external prosthetic ring having elastic, fluid-fillable chambers supported by mechanical abutments, essentially inelastic plates, for cardiac assist purposes. The device described includes a plurality of fluid fillable chambers, and can be engineered to apply local pressure on part of the heart only, such as to the left ventricle, for example.

U.S. Pat. No. 6,251,061 to Hastings et al. describes a cardiac assist device using field controlled fluid. U.S. Pat. No. 6,508,756 to Kung et al. describes yet another cardiac assist device that may be active or passive.

Prior art cardiac assist systems described hereinabove suffer from a common drawback in that the diseased heart is subjected to a sudden external contracting force. This is somewhat unnatural and may be a contributory factor to the low life-expectancy of recipients using such systems.

Prior art for leg massaging includes U.S. Pat. No. 5,672,148 to Maunier, which describes a hydraulic device for lymphatic drainage and massage of the human body that comprises a chamber with outer quasi-rigid & inner supple walls, filled with porous material through which a viscous fluid is circulated. The device provides hydrostatic pressure around the limb and does not provide different pressures to different areas.

U.S. Pat. No. 5,437,610 to Cariapa et al. describes an extremity pump apparatus for the treatment of edema. A plurality of bladders arranged in a bandage for wrapping around a limb is described. The closing arrangement allows the bandage to be fitted to limbs of different sizes. The plurality of bladders is connected via a manifold and valves to a hydraulic pressure source. The prosthetic is either cylindrical or frustoconical.

U.S. Pat. No. 6,589,194 to Calderon et al. describes a device, essentially a boot, for promoting circulation by externally massaging a leg. The chambers thereof are air-filled. The pumping action is activated by movement of the wearer, particularly by wearer transferring weight from one foot to another.

SUMMARY OF THE INVENTION

It is an aim of the present invention to provide an organ assist system and method, by means of the localized application of pressure to portions thereof, thereby to support the operation of an assisted organ.

Preferred embodiments of the present invention address this aim by providing a novel hydraulic physiological pressurization system for aiding blood circulation, particularly for use as a cardiac assist device. It will, however be appreciated that other, appropriately configured embodiments of the present invention are applicable for other applications, such as for leg massage for diabetics, for example.

There is thus provided, in accordance with a preferred embodiment of the invention, an organ assist system which includes:

(I) a closed hydraulic system of recirculating fluid which has
  (i) a ring-shaped prosthetic that contactively surrounds at least a portion of the body part, including a plurality of bladders adapted for selectable dilation and contraction in response to a varying fluid pressure therewithin;
  (ii) a fluid pump;
  (iii) a pressurization apparatus, and
  (iv) conduits connecting the bladders, pump and pulsation apparatus, and
(II) a control system including:
  (a) a control unit for controlling operation of at least the fluid pump;
  (b) a plurality of pressure sensors within the closed hydraulic system;
  (c) a power source for powering the control system, and
  (d) a plurality of shut off valves;
wherein the pressurization apparatus includes a plurality of pressure cells arranged in an array, each pressure cell having controlled shut-off valve at the inlet thereinto, and a second controlled shut-off valve at the exit therefrom, the controlled shut-off valves being controlled by the control unit of the control system such that the pressurization apparatus may provide a range of pressurizations to the bladders of the prosthetic for applying a controlled variable pressurizing effect to the body part thereby.

Additionally in accordance with a preferred embodiment of the invention, the pressurization apparatus includes a plurality of N pressure cells, and being capable of providing up to $2^N$ pulse intensities to bladders of the prosthetic.

Further in accordance with a preferred embodiment of the invention, the pressurization apparatus includes an array of N pressure cells, operable in at least one of the following modes:
  parallel,
  series, and
  a combination of parallel and series.

Additionally in accordance with a preferred embodiment of the invention, the including two arrays of the pressure cells, positioned upstream and downstream, respectively, relative to the ring-shaped prosthetic.

Further in accordance with a preferred embodiment of the invention, each pressure cell includes a cage of a substantially rigid biocompatible material divided into an inner chamber and an outer chamber by a flexible elastic wall, the outer chamber being a sealed chamber bounded by the cage and the flexible elastic wall and being filled with a low-density gas, and the inner chamber being defined by the flexible elastic wall, having an inlet and an outlet that are closable by fast action valves.

Additionally in accordance with a preferred embodiment of the invention, the flexible elastic wall is a tube of a flexible elastic material within the cage.

Further in accordance with a preferred embodiment of the invention, wherein desired pressurizations are obtainable from each the pressure cell with high accuracy by appropriate selection of volume of the sealed cage and control of pressure therein.

Additionally in accordance with a preferred embodiment of the invention, the outer chambers of each of at least two of the plurality of pressure cells has a different size and/or a different internal pressure.

Further in accordance with a preferred embodiment of the invention, outer chambers of each of the plurality of pressure cells are connected to a reservoir, such that minimum pressure within outer chamber, corresponding to a fully flattened inner chamber, is variable.

Additionally in accordance with a preferred embodiment of the invention, the prosthetic includes a plurality of components including conduits and bladders, selectable from a kit to provide a specific prosthetic adaptable to a specific body part of a specific patient.

Further in accordance with a preferred embodiment of the invention, the prosthetic has a modular construction and includes individual conduits, bladders and rigid backing plates, for arranging around the body part, in one or more layers thereby allowing tailoring of the prosthetic to a specific organ of a specific patient.

Additionally in accordance with a preferred embodiment of the invention, the prosthetic is tailored to fit a specific organ of a specific patient by selecting and arranging appropriate sub-components to provide appropriate pressure characteristics locally where needed.

Further in accordance with a preferred embodiment of the invention, the body part is a heart and the prosthetic is a heart engaging prosthetic that surrounds at least a part of the heart.

Additionally in accordance with a preferred embodiment of the invention, the system also includes an ECG sensor coupled to the control unit to control the shut-off valves of the system in response to the pumping of the heart.

Further in accordance with a preferred embodiment of the invention, the system is configured as a heart assist device for assisting a damaged heart to pump, wherein the plurality of pressure cells provides a diastolic pressure to prevent the relaxed heart from dilating.

Additionally in accordance with a preferred embodiment of the invention, the system is configured as a heart assist device for assisting a damaged heart to pump, wherein the plurality of pressure cells provides a systolic pressure to assist the contraction of the heart and thus assist the pumping thereof.

Further in accordance with a preferred embodiment of the invention, the body part is an internal organ and the control system is powered by a transcutaneous energy transmission (TET) system.

Additionally in accordance with a preferred embodiment of the invention, the control unit is programmable prior to activation and/or during operation.

Further in accordance with a preferred embodiment of the invention, the control unit is responsive to changing needs.

Additionally in accordance with a preferred embodiment of the invention, wherein the fluid is saline.

There is also provided, in accordance with a further embodiment of the present invention, a pressurization apparatus for an organ assist system having a ring-like prosthetic formed of a plurality of fluid expansible bladder portions for applying pressure to a body organ on which the prosthetic is mounted, the pressurization apparatus including:
an array of fluid expansible pressure cells, each having an inlet and an outlet;
a first shut-off valve arranged at the inlet of each the pressure cell;
a second shut-off valve arranged at the outlet of each the pressure cell; and
a control unit for selectably operating each of the first and second valves, so as to operate the pressurization apparatus in providing a range of pressurizations to the bladder portions of the prosthetic for applying controlled variable pressures to the body organ thereby.

Further in accordance with the present embodiment, there are provided N pressure cells capable of providing up to $2^N$ pulse intensities to bladders of the prosthetic.

Additionally in accordance with the present embodiment, the pressurization apparatus includes an array of N pressure cells, operable in at least one of the following modes:
- parallel,
- series, and
- a combination of parallel and series.

Further in accordance with the present embodiment, the system includes two arrays of pressure cells, positioned upstream and downstream, respectively, relative to the ring-shaped prosthetic.

There is further provided a pressure cell for use within the above system, the pressure cell including a cage of a substantially rigid biocompatible material divided into an inner chamber and an outer chamber by a flexible elastic wall, the outer chamber being a sealed chamber bounded by the cage and the flexible elastic wall and being filled with a low-density gas, and the inner chamber being defined by the flexible elastic wall, having an inlet and an outlet that are closable by fast action valves.

Additionally in accordance with the present embodiment, the flexible elastic wall is a tube of a flexible elastic material within the cage.

Further in accordance with the present embodiment, the sealed cage has a volume predetermined to facilitate provision of a predetermined maximum pressure by the pressure cell.

Additionally in accordance with the present embodiment, the outer chambers of the pressure cell are connected to a fluid reservoir, such that minimum pressure within outer chamber, corresponding to a fully flattened inner chamber, is variable.

Further in accordance with the present embodiment, the minimum pressures within the cell and the pumping cycle thereof, is controllable by a programmable microprocessor.

In accordance with an additional embodiment of the invention, there is provided a prosthetic for engaging a body part, for applying a pressurizing effect to the body part, the prosthetic including a plurality of components including conduits and bladders, the components being selectable from a kit to provide a specific prosthetic adaptable to a specific body part of a specific patient.

Additionally in accordance with the present embodiment, the prosthetic has a modular construction and includes a number of individual conduits, bladders and rigid backing plates, for arranging around the body part, in one or more layers thereby allowing tailoring of the prosthetic to a specific organ of a specific patient.

Further in accordance with the present embodiment, the prosthetic is tailored geometrically to the specific organ of the specific patient by selecting and arranging appropriate sub-components to provide appropriate pressure characteristics locally where needed.

Additionally in accordance with the present embodiment, the body part is a heart and the prosthetic is a heart engaging prosthetic that surrounds at least a part of the heart.

Further in accordance with the present embodiment, there is also provided apparatus for harnessing the prosthetic about a heart, wherein the apparatus for harnessing harnesses about upper and lower regions of the heart so as to squeeze the heart in response to a contraction of the prosthetic.

Additionally in accordance with the present embodiment, the prosthetic is configured as a heart assist device for assisting a damaged heart to pump, wherein the prosthetic is coupled to a plurality of pressure cells to provide a diastolic pressure to prevent a relaxed heart from dilating.

Further in accordance with the present embodiment, the prosthetic as a heart assist device for assisting a damaged heart to pump, wherein the prosthetic is coupled to a plurality of pressure cells to provide a systolic pressure to assist the heart to contract and thereby assist its pumping.

There is yet further provided, in accordance with the invention, a method of applying a controlled, variable pressure to a body part using the system of claim 1, by activating the shut-off valves of the pressure cells of the pressurization apparatus in accordance with an algorithm.

In accordance with yet one further embodiment of the invention, there is provided a modular organ engaging prosthetic including a plurality of individual conduits, manifolds, bladders and rigid backing plates, for arranging around the organ, in one or more layers thereby allowing tailoring of the prosthetic to a specific organ of a specific patient.

BRIEF DESCRIPTION OF THE DRAWINGS

The present invention will be more fully understood and appreciated from the following detailed description, taken in conjunction with the drawings, in which:

FIGS. 5A-5C are schematic illustrations of the structure of the cardiac prosthetic illustrated in FIG. 4, in which FIG. 5A is a cross-section through the wall of the prosthetic in a relaxed state, FIG. 5B is the same cross section wherein the bladders thereof are fully dilated, and FIG. 5C is an elevational view of the inward-facing surface of the prosthetic, in the direction indicated by arrow 5C in FIGS. 4, 5A and 5B;

FIG. 4 is a schematic view of a torroidal cardiac prosthetic in accordance with another embodiment of the invention;

Figure 1A:
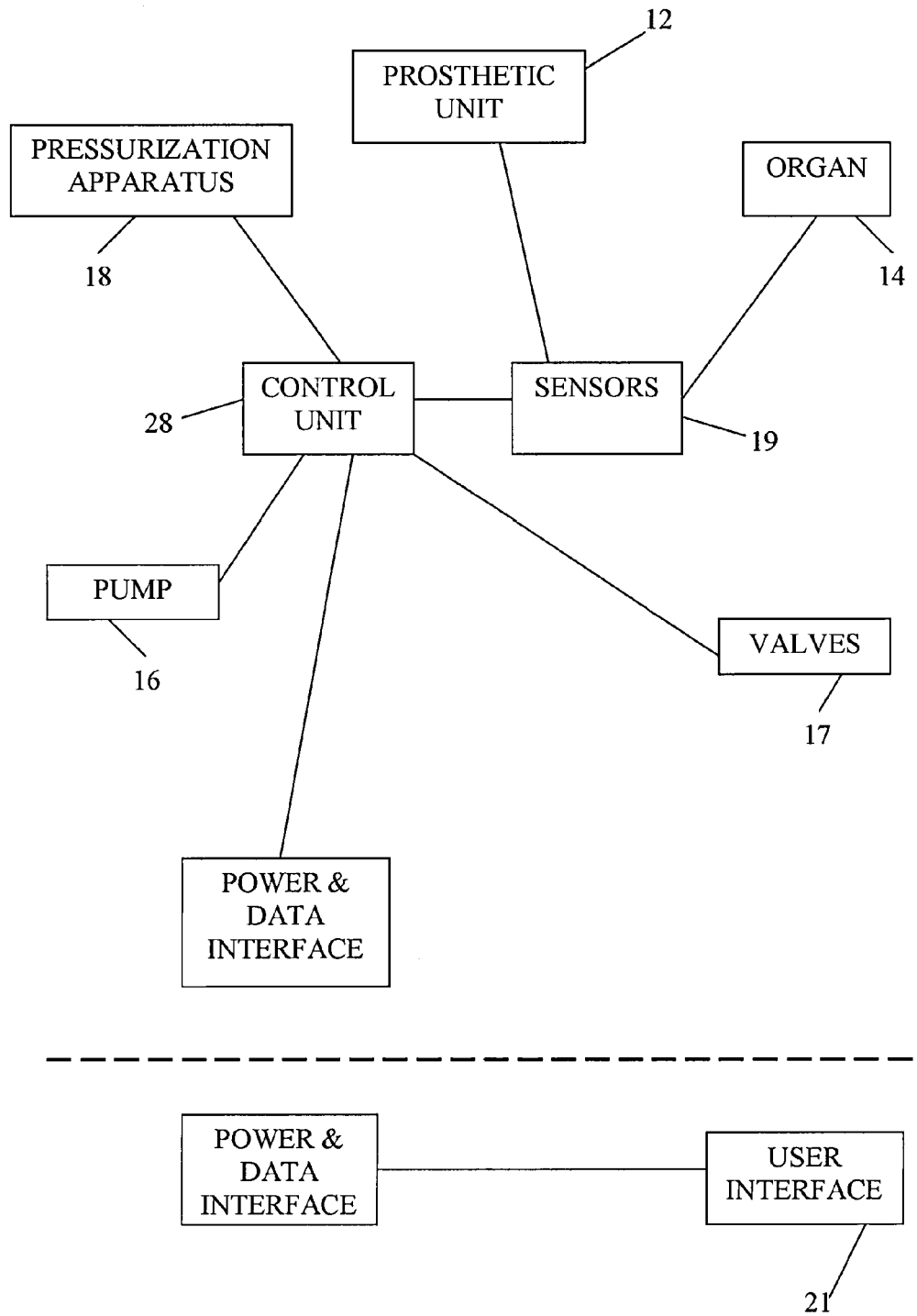
FIG. 1A is a block diagram representation of an organ assist system, constructed and operative in accordance with a preferred embodiment of the present invention.
Figure 1B:
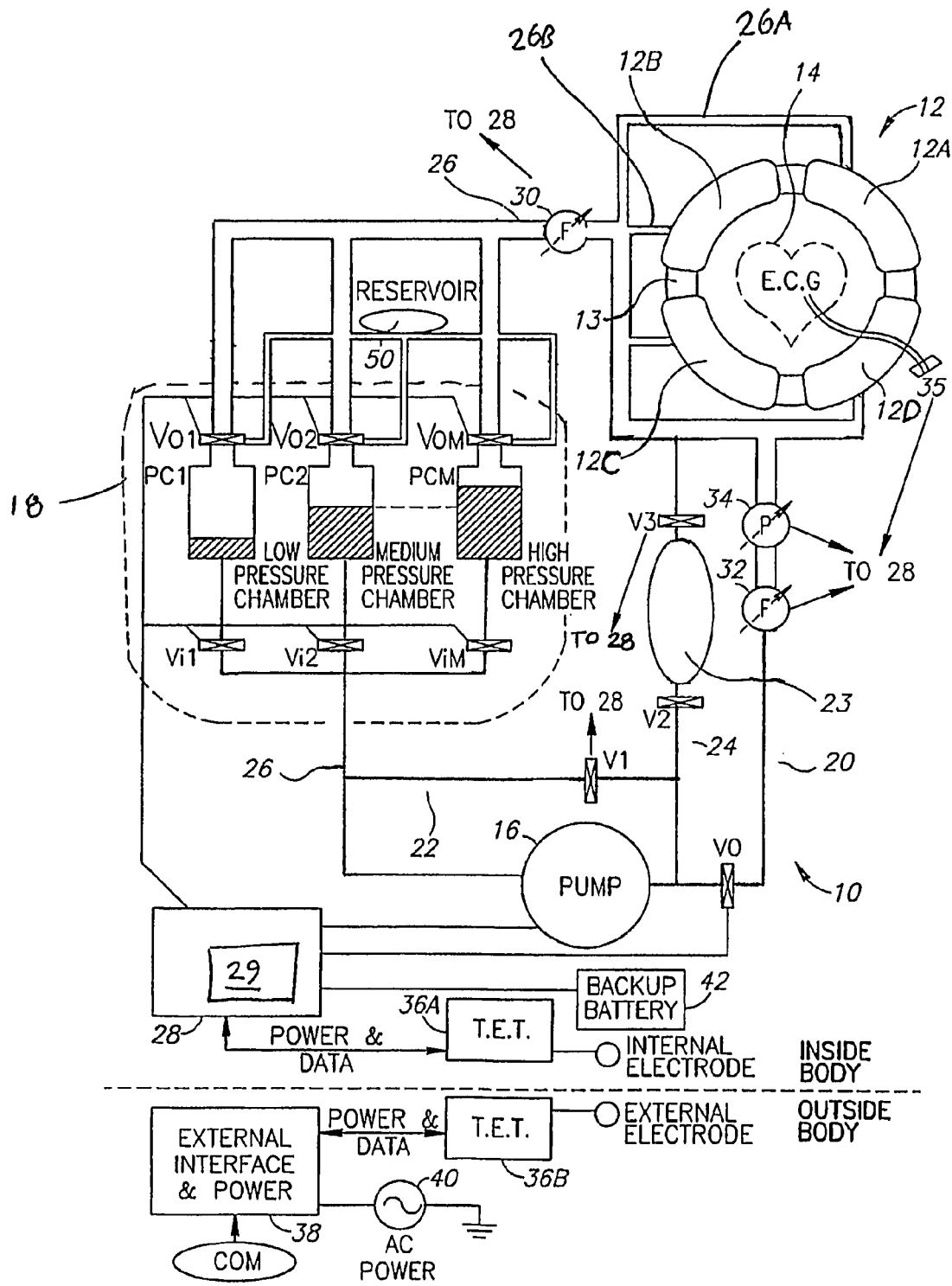
FIG. 1B is a schematic illustration of the present invention, exemplified as a cardiac assist system, constructed and operative in accordance with a preferred embodiment of the present invention.

Graph (A) is a typical ECG plot (micro-volt versus time) for a heart;

Graph (B) is a corresponding Cartesian representation of the pumping cycle of the pumping mechanism of the mechanical pump of the heart assist device in a corresponding time scale to (A);

Graph (C) is a pressure versus time plot for the bladders of the exemplary heart assist prosthetic in accordance with a generalized embodiment of the present invention;

Graphs (D), (E), and (F) are digital time plots for the low pressure, medium pressure and high-pressure valves respectively;

Graph (G) is a digital time plot for the pump self circulation valve $V_1$ of the generalized cardiac assist system of FIG. 1B;

Graph (H) is a digital time plot for the main refill valve $V_2$ of the cardiac assist system of FIG. 1B, and Graph (I) is a digital time plot for the second refill valve $V_0$ of the generalized cardiac assist system of FIG. 1B.

DETAILED DESCRIPTION OF THE INVENTION

With specific reference now to the drawings in detail, it is stressed that the particulars shown are by way of example, for purposes of illustrative discussion of the preferred embodiments of the present invention, and are presented in the cause of providing what is believed to be the most useful and readily understood description of the principles and conceptual aspects of the invention. In this regard, no attempt is made to show structure in more detail than is necessary for a fundamental understanding of the invention.

The description, taken with the drawings make apparent to those skilled in the art, show how preferred embodiments of the present invention, directed to providing a practical apparatus device and system for tailoring an organ assist system, and particularly a heart assist system, to a particular, may be configured.

Post-cardiotomy cardiogenic shock is one type of heart failure that may result from heart surgery. It is believed that the sudden application of a systolic squeezing force to a heart by a heart assist device, may apply a shock and cause trauma to the susceptible heart tissue of a damaged heart. In addition to providing a mechanical and geometrically adaptable heart assist that provides pressure where needed, it is a particular feature of preferred embodiments of the invention that the pressure applied to the heart is built up in stages, in a manner that more appropriately matches physiologic requirements than that provided by prior art systems.

Referring now initially to FIG. 1A, there is shown, in block diagram form, an implantable organ assist system, constructed and operative in accordance with a preferred embodiment of the present invention.

The system includes an organ engaging prosthetic 12, which applies an external pressure to at least a portion of a dysfunctional organ or limb 14. The cardiac engaging prosthetic 12 is connected in series with a fluid pump 16 and fluid pressurization apparatus 18, described in detail hereinbelow, inter alia, in conjunction with FIGS. 1B, 2, 3A, 3B, and 6A-6C. A control unit 28 is employed to operate the prosthetic 12 by means of pump 16 and plurality of valves 17 arranged throughout the system, so as to selectively pressurize or depressurize the pressurization apparatus 18, and thus to correspondingly pressurize or depressurize different inflatable portions of the prosthetic 12, as described hereinbelow in detail. A plurality of sensors 19, are also provided, both for monitoring the system and the organ 14; control unit 28 is programmed to vary the operation of the prosthetic 12, in accordance with the requirements of the patient, and in response to readings from the sensors 19.

There is also provided a preferably a transcutaneous pair of power and data interfaces, described hereinbelow in detail, as well as a user interface 21, on which data may be displayed to a user, such as the physician or patient, and via which the physician may input data or program commands.

Referring now to FIG. 1B, a generalized block diagram showing the basic components of system 10 when constructed as a typical cardiac assist system, constructed and operative in accordance with a preferred embodiment of the present invention. The system 10 includes a cardiac engaging prosthetic 12, which applies an external pressure to at least a portion of a dysfunctional heart 14. The cardiac engaging prosthetic 12 is connected in series with a pump 16 and pressurization apparatus 18, typically including a plurality of pressure cells $PC_1$, $PC_2$, ... $PC_m$, illustrated in the present example as being in a mutually parallel arrangement. There are also provided shut off valves V, more specifically a first shut-off valve $V_0$ that closes the outlet pipe 20 leading away from the cardiac engaging prosthetic 12 and a second shut off valve $V_1$ located in a bypass conduit 22 that enables the pump 16 to be bypassed thereby. Optionally third and fourth shut-off valves $V_2$, $V_3$ are provided to isolate from or to connect to the system 10 an optional fluid reservoir 23 via a conduit 24, so as to control the effective amount of recirculating liquid in the system 10, and the ambient pressure therein. Each pressure cell $PC_n$ of the plurality of pressurization apparatus 18 has an inlet shut off valve $V_{i1}$, ($V_{i2}$ ... $V_{im}$) at its inlet, for controlling the flow of liquid thereinto, to isolate the pressure cells PC from the conduit 25 that connects same to the pump 16. Similarly, shut off valves $V_{o1}$, $V_{o2}$ ... $V_{om}$) are provided at the outlets of the pressure cells $PC_1$, $PC_2$ ... $PC_m$, for controlling the flow of the feed of fluid therefrom, via an outgoing fluid bus 26 that feeds into the cardiac engaging prosthetic 12. The pump 16 and valves V are coupled to a control unit 28 that controls their operation, typically in accordance with a set of instructions determined by the surgeon or doctor in whose care the patient lies, and usually in response to a plurality of sensors that monitor the system 10 and the heart 14. Such sensors include flow meters 30, 32 that monitor the flow of fluid to and from the cardiac engaging prosthetic 12; one or more pressure gauges 34 for monitoring the fluid pressure in the system, and an ECG sensor 35 attached to the heart 14 itself, for monitoring vital statistics thereof. The sensors are coupled to the control unit 28, usually by wires—not shown for clarity. Control unit 28 normally includes a microprocessor 29, as well as other required hardware and software such as may be required to operate system 10 in accordance with the present invention.

In consequence of the ECG 35 and the pressure and flow sensors 30, 32, 34, the physical activity of the heart 14 and of the system 10 are tracked, thereby providing real time information of the pumping activity over time, enabling adaptation to be made to the system 10 as and where necessary, for example.

The ECG sensor 35 provides vital information regarding the heart's activity and is particularly useful for detecting irregularities thereof. By being coupled with the control unit 28, sensor 35 may be used to synchronize the contractions of the cardiac engaging prosthetic 12 with the actual requirements of the heart 14, and provides warning of heart failure and major irregularities, thereby indirectly providing warning of poor functioning and possibly failure of the system 10. Preferably it automatically triggers a pressure relaxation in the cardiac engaging prosthetic 12 in case of such a failure by opening or closing the various valves to their fail safe positions.

The cardiac engaging prosthetic 12 typically includes a plurality of inflatable segments 12A-12D, each having one or more inflatable bladders inflatable by pumping thereinto a fluid, typically saline solution. The fluid is pumped in a closed loop around the conduits 20, 22 and optionally 24, as well as through fluid bus 26. Bladders 12A-12D are typically coupled together via appropriate lengths of webbing, tubing or the like, referenced 13.

Figure 1C:
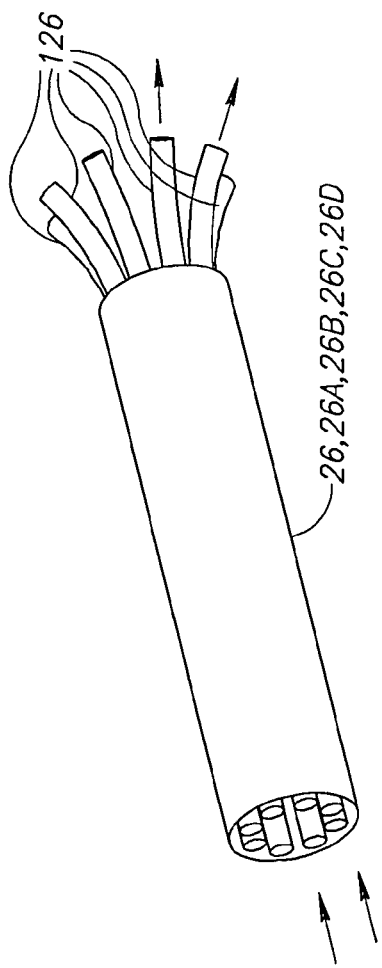
FIG. 1C is a schematic illustration of a portion of a fluid bus employed in the system of the present invention.

Fluid bus 26 divides into four smaller buses, respectively referenced 26A-26D, for supplying each of bladders 12A-12D, respectively. As will be appreciated from the description hereinbelow of these bladders, in conjunction with FIGS. 5A-5C, and FIGS. 6A-6C, each pressure cell PC may be connected to multiple bladders, or each bladder may be supplied by a plurality of pressure cells, in accordance with specific system requirements. Accordingly, and referring now briefly to FIG. 1C, it is seen that fluid buses 26 and 26A-26D carry a plurality of fluid conduits 126, so as to properly supply each bladder with pressurized fluid, as necessary. It will thus also be appreciated that the above described sensors 30, 32 and 34, may actually be replaced by a plurality of sensors at each sensor location illustrated in FIG. 1B, as may be required in any system configuration, so as to determine the fluid flow rate and fluid pressure in each fluid conduit 126, as necessary.

The pump 16 may be any suitable rotary or piston pump suitable for pumping fluid. In preferred embodiments, system 10 of the invention described above, including the pump 16 and the pressurization apparatus 18 is implanted within the patient. To facilitate this, it is contemplated that a transcutaneous energy transmission (TET) system 36 composed of internal and external coils 36A, 36B be used to transmit power across the skin. Such a system is in current use with prior art systems such as the AbioCor described hereinabove. TET systems 36 are advantageous in that the likelihood of developing an infection therewith is low because tubes and wires do not pass through the skin.

Power and data is supplied to the external TET 36B from an external interface and power supply 38, that typically includes external battery packs that may be recharged by coupling to a mains power supply 40, for example. A backup battery 42, which may be long life or rechargeable, allows the external power supply 38 to be disconnected, such as to allow patient to bathe, for example.

Valves $V_n$ of the system may be fast-action rotary valves, such as that described in U.S. Pat. No. 5,713,954, incorporated herein by reference, see column 5 line 55 and column 12 lines 31-52 thereof, for example. Other suitable types of valve include modifications of cardiac valves of the prior art, such as Wada Cutter valves, Bjork-Shiley valves and trileaflet valves, for example.

As stated hereinabove, in the various embodiments, the pressurization apparatus 18 includes a plurality of pressure cells (referenced $PC_1$, $PC_2$ ... $PC_m$ in FIG. 1B).

Figure 3A:
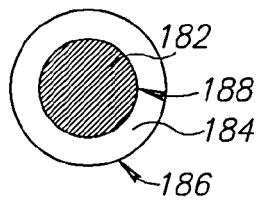
FIGS. 3A and 3B show an exemplary pressure cell of the present invention in cross-sectional and isometric views respectively.
Figure 3B:
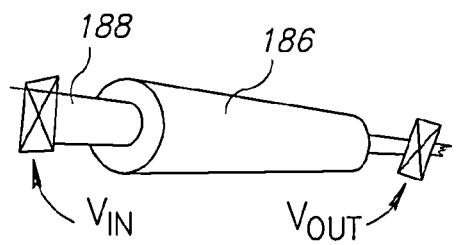

Referring now to FIGS. 3A and 3B, a single pressure cell PC includes an elastic walled inner chamber 182 within an external, rigid walled outer chamber 184, having an outer sleeve or cage 186 of a rigid biocompatible material such as high-density polyethylene, silicone, titanium or stainless steel, for example. Within the outer sleeve 186, an inner sleeve 188 of a flexible elastic material such a soft silicone is provided. The space between the inner 188 and outer 186 sleeves is filled with a low-density gas such as nitrogen or helium and is effectively sealed. The inner sleeve 188 is closable at the inlet and outlet of the pressure cell PC by fast action valves $V_{IN}$, $V_{OUT}$ such as those described in U.S. Pat. No. 5,713,954, that operate in turn to pump a high density fluid, typically saline, through the pressure cell PC. The inner chamber 182 of the pressure cell PC sits along a closed liquid loop and out of step closing and opening of the valves $V_{IN}$, $V_{OUT}$ at inlet and outlet thereof in turn circulates liquid around the closed liquid loop, by means of a peristaltic-type pulsing action. The closed liquid loop is typically filled with a biocompatible, substantially non-compressible liquid such as saline, and, referring back to FIG. 1B, operation of the inlet and outlet valves $V_i$ and $V_o$ of the pressure cell PC under control of the control unit 28, forces the liquid around the loop. The pulses of liquid exert a dilating effect on the bladder segments 12A, 12B, 12C, 12D of the heart engaging prosthetic 12 connected therewith, and apply a squeezing force to the heart 14 thereby.

It is a particular feature of the present invention that a plurality of such pressure cells PC is provided; each capable of delivering a specific pulse, depending on the pressure within the outer chamber 184 (FIG. 3A), and the volume thereof. The maximum pressure that may be applied by each pressure cell PC is defined by the geometry thereof and by the pressure in the closed outer chamber 184, which are design parameters that are well controlled. In consequence, use of pressure cells of this type has little risk to the patient. It should also be noted, as described hereinbelow, that the maximum pressure which each pressure cell develops may be adjusted by appropriate means.

It will be appreciated that the actual pressure applied by each pressure cell PC will depend on control variables, in particular, the time interval between the opening and closing of the inlet and outlet valves $V_{IN}$, $V_{OUT}$ and the pressure of the system, which, in some embodiments, may itself be varied via the reservoir 23.

At least two such pressure cells, i.e. a low-pressure cell and a high-pressure cell may be provided, or, as shown in FIG. 1B, three or more such chambers $PC_1$, $PC_2$ $PC_m$ may be provided. Essentially, the pressure generated by the low-pressure cell provides a compressive force that contains an expanded heart or applies a first pressure that acts with the pumping of the diseased heart. The higher pressure is then introduced to help the heart contract. Where a plurality of pressure cells are provided, the pressure may be built up gradually, thereby minimizing the shock applied to the weakened heart, which is one disadvantage of prior art systems.

It will be appreciated that two cells capable of applying dilatory force of P1 and P2 respectively, can actual provide ($2^2$) four different pressures, i.e. 0, P1, P2, and an additional pressure f(P1P2)—the magnitude thereof depending on the way in which the two pressure chambers are coupled. Where a larger number of pressure cells are provided, the pressure may be built up more gradually. In some embodiments, a plurality of such pressure cells are connected in series to feed into the same bladder(s) of the organ engaging device, to provide a variable controlled pulse thereto, and typically a gradually increasing pulse. In a second embodiment, a plurality of pressure cells is connected each to a separate bladder or ring of bladders arranged in parallel around the heart, perhaps in concentric rings, thereby allowing application of separate pulses to different bladders individually or in unison, again allowing variable dilatory forces to be applied to the heart thereby.

Figure 4:
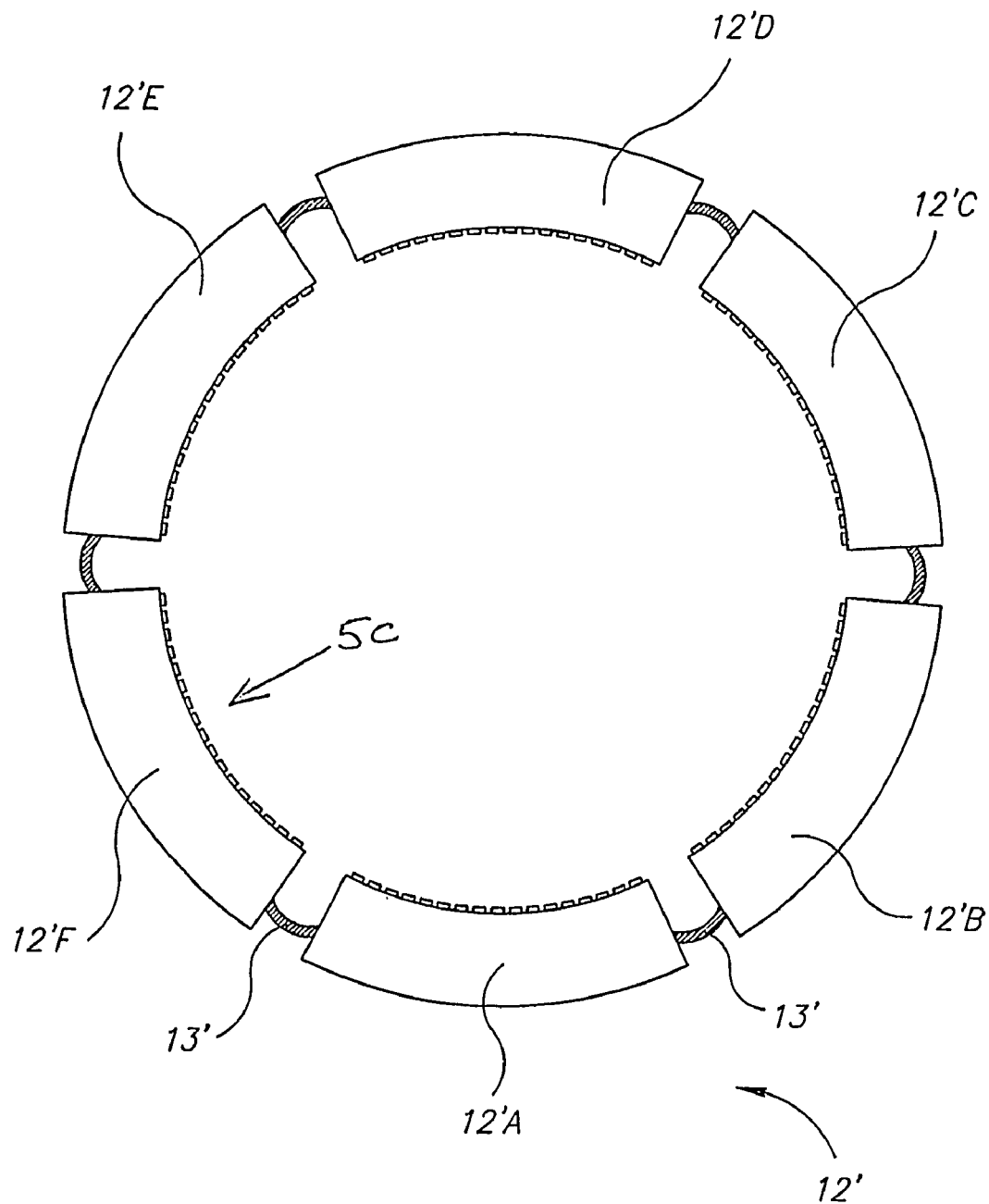
FIG. 4 is a schematic view of a torroidal cardiac prosthetic, constructed in accordance with a preferred embodiment of the present invention.

Referring now to FIG. 4, in a preferred embodiment of the invention, the prosthetic 12 includes a plurality of units 12'A-12'E that may be connected and disconnected via conduit sections 13 of various lengths, that may themselves be cut to size, to provide a geometric fit to the size of the organ to be pressure treated, possibly applying a physical restraint to an enlarged heart at all times. This modular structure allows the prosthetic 12 of the present invention to be accurately tailored to specific hearts, even during surgery; it being appreciated that even healthy hearts vary enormously between individuals, and damaged hearts, even more so.

Figure 5B:
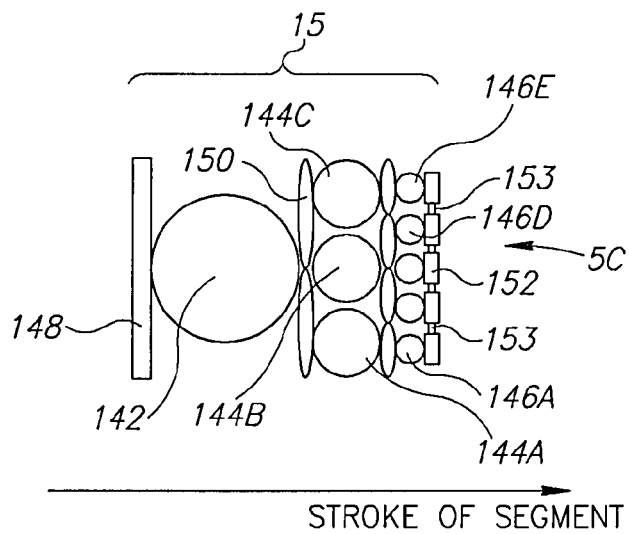
Figure 5C:
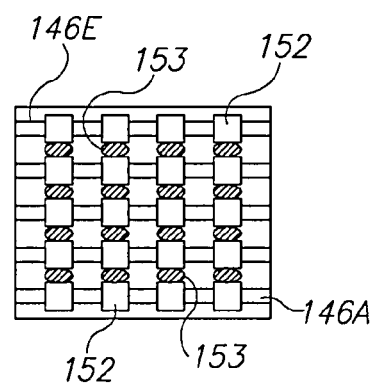
Figure 5A:
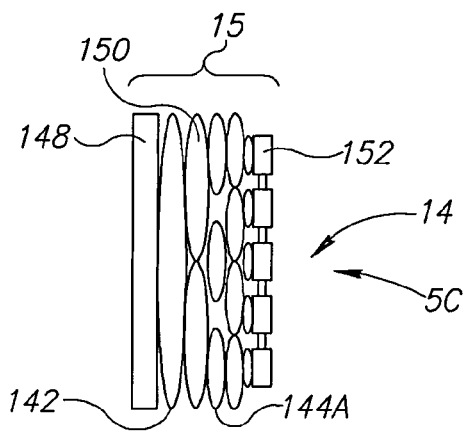

Referring to FIGS. 5A-5C, there is detailed the construction of the wall 15 of a cardiac engaging prosthetic 12 in accordance with an embodiment of the present invention. The wall 15 of the prosthetic 12 includes a plurality of hydraulically inflatable bladders 142, 144A-C, 146A-E, formed typically of soft silicone or similar, in which the bladders are arranged, in part, in multiple layers with rigid plates 148, 150, 152 therebetween, and may be physically tailored to a particular heart thereby. Plates 148, 150 and 152 are typically formed of a relatively rigid silicone, or similar material. Inward-facing plates 152 are linked together, as seen in FIG. 5C, by semi-rigid link elements 153, typically formed of semi-rigid silicone. FIG. 5A shows the wall 15 with the bladders thereof deflated, and FIG. 5B shows the wall in its expanded state with the bladders thereof inflated, as would apply a compressive force on a heart or limb. The individual bladders may be inflated together or in turn, depending on how they are coupled to the pressurization apparatus 18 and to the number of pressure cells 18' thereof, which may be coupled one-on-one, or all pressure cells 18A-18N to all bladders 142, 144A-C, 146A-E via manifolds, or to some intermediate combination.

In accordance with a preferred embodiment of the invention, there is also provided harnessing means for retaining the prosthetic 12 in pressure-contact with the organ being treated, the harnessing means including straps, walls and other elements, which may be pressurizable and/or elastic and/or inelastic, as required.

Figure 7:
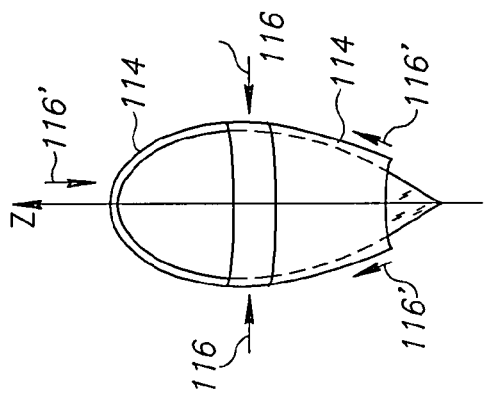
FIG. 7 is a schematic illustration showing a typical manner in which the prosthetic of the invention may be secured to a heart.

Such an arrangement is illustrated schematically in FIG. 7, in which there is seen a prosthetic 12 of the present invention which is strapped to a heart 14. The strapping 114 is preferably composed of bio-compatible elements, such as silicon, which are used to harness the prosthetic 12 to the heart 14 so as to prevent slippage along the illustrated Z axis.

It will be appreciated that in the arrangement illustrated in FIG. 7, as a consequence of the harnessing as shown and described, inflation of individual bladders as indicated by arrows 16 may result in tensile forces being applied to the harnessing means 114, thus causing pulling forces, indicated by arrows 116', to be applied to the heart so as to cause a squeezing thereof the heart, and so as to assist in its pumping. Particularly, it will be noted that dilation of bladders around the top of the heart may apply a pulling force on the bottom of the heart.

The structures shown in FIGS. 4A-5C exemplify one possible configuration of prosthetic 12 only. It is a feature of preferred embodiments of the prosthetic of the present invention that the prosthetic is modularly constructed from elements such as manifolds, conduits, bladders, rigid plates and the like, coupled together to form a ring-, cylindrical-, frustoconical- or cup-shaped structure to fit and apply pulsating forces to a heart or other organ requiring massaging. Since local dilatable bladders are provided, it is possible to provide a pumping force to a specific location on heart, such as on one or other ventricle or over-weakened muscle, or in general, different assistive forces in different locations. Indeed, via various features such as the multilayer structure of prepared embodiments (see FIGS. 5A and 5B), and/or the multiple pressure cells $PC_n$ and/or the reservoir 23 for example, different forces may be applied to the same region of the heart, via the same segment (e.g. 12A—see FIG. 1B) of the heart assist device.

In general, therefore, design parameters, such as the geometry of the pressure cells, prevent maximum allowable pressures from being exceeded, with control variables determining the actual pressures applied.

It is a particular feature of preferred embodiments in that the heart assist device may be physically adapted to fit specific patients, perhaps being constructed from a kit of components that may be selectively coupled together, thereby providing a tailored solution for the exposed diseased heart of a patient during the operation.

Figure 1D:
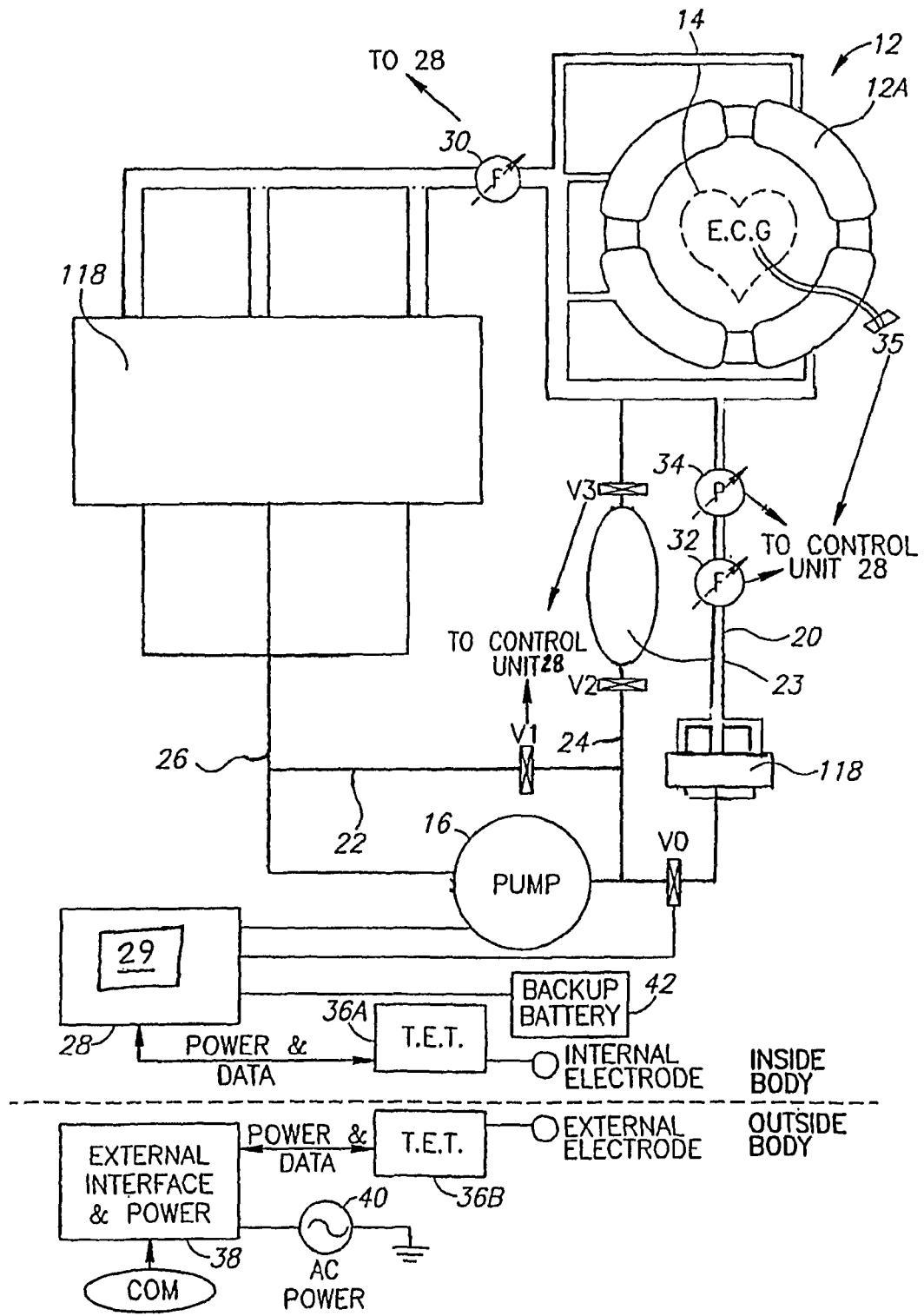
FIG. 1D is a schematic illustration of a generalized cardiac assist system, constructed and operative in accordance with an alternative embodiment of the present invention.
Figure 2:
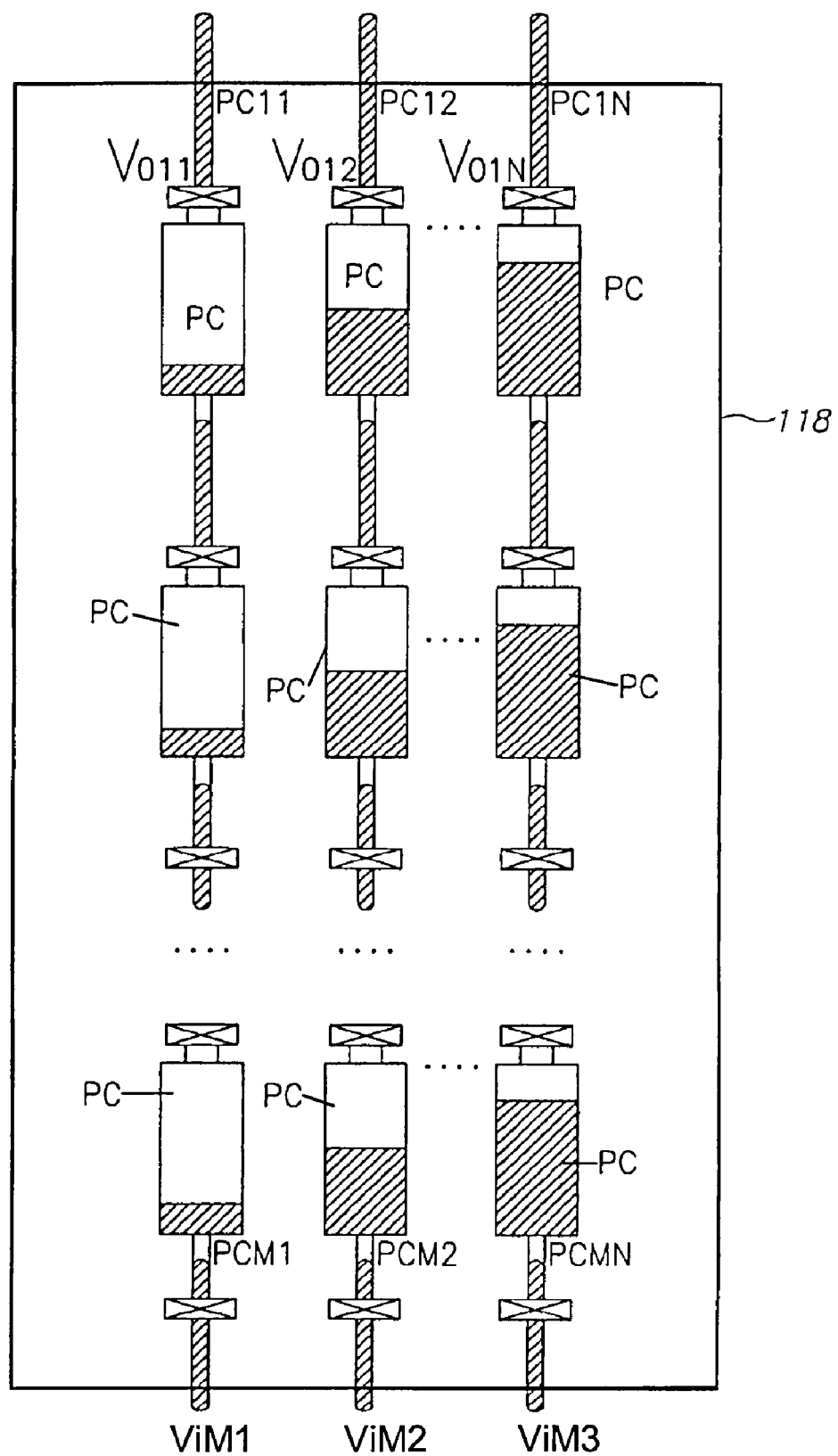
FIG. 2 is a schematic depiction of an array of pressure cells employed in the cardiac assist system of the present invention, in accordance with a further embodiment of the present invention.

Referring now briefly to FIG. 1D, there is illustrated a cardiac assist system, substantially similar to that shown and described herein in conjunction with FIG. 1B, but having one or two pressurization apparatus blocks 118, upstream or downstream of prosthetic 12, as may be deemed necessary in any specific construction. Furthermore, as illustrated in FIG. 2, each pressure block may be formed as a matrix array of pressure cells PC, in which any combination of pressure cells in series and/or in parallel may be employed so as to obtain a desired control of the prosthetic 12, in operation.

Figure 6B:
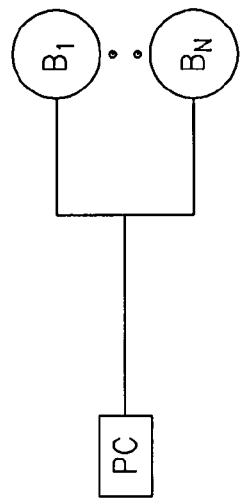
FIG. 6B is a diagram showing operation of a plurality of prosthetic bladders by a single pressure cell.
Figure 6C:
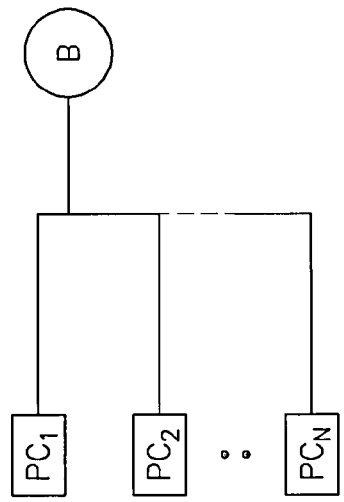
FIG. 6C is a diagram showing operation of a single prosthetic bladder by a plurality of pressure cells.
Figure 6A:
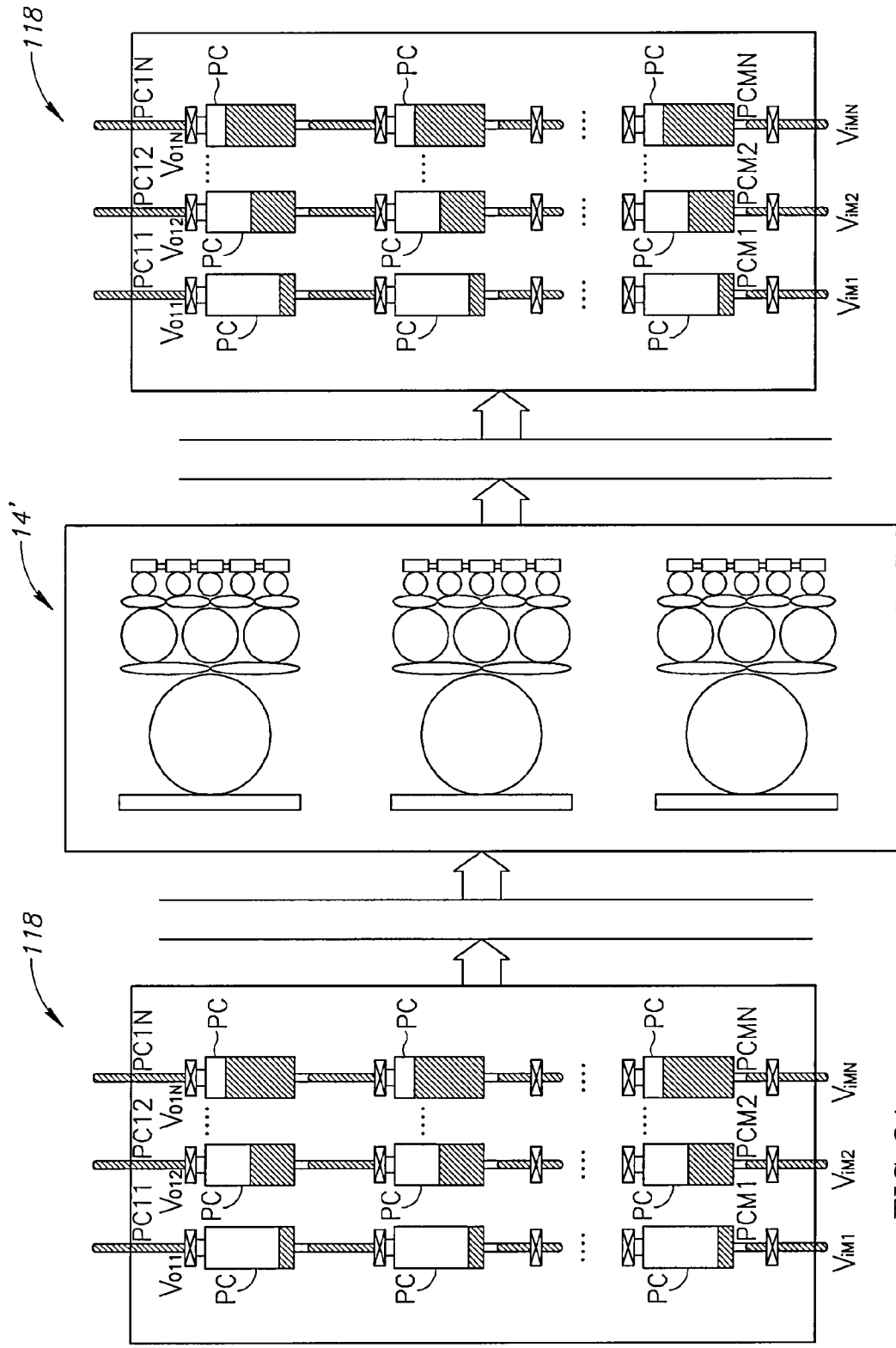
FIG. 6A is a diagram of a dual matrix, large scale distribution and interleaving valve diagram, employable in the system of the present invention.

Referring now also to FIG. 6A, which is a diagram of a dual matrix, large scale distribution and interleaving valve diagram, employable in the system of the present invention, it will be appreciated that the system of the invention in an extremely high-resolution system in which a specific solution may be provided for a specific patient, so as to pressurize specific areas of his or her body organ, precisely as required.

By way of example, and with reference to FIGS. 6B and 6C, it is clearly seen that the matrix construction of the pressurization apparatus 18 of the present invention provides for many different fluid supply arrangements for each pressure cell PC and each bladder or bladder portion B. Accordingly, FIG. 6B represents a one-to-many arrangement, in which a plurality of prosthetic bladders $B_1, \ldots, B_N$ are pressurized by a single pressure cell PC, while FIG. 6C represents a many-to-one arrangement, in which a single prosthetic bladder B is pressurized by a plurality of pressure cells $PC_1, \ldots, PC_N$.

FIG. 7 is a schematic illustration showing a typical manner in which the prosthetic of the invention may be secured to a heart;

It will thus be appreciated that the number and capacities of the pressure cells may be selected to provide a patient-specific range of pressures with an appropriate number of intermediate layers. Individual pressure cells may be arranged in series or in parallel, as shown and described above, and upstream and/or downstream of the prosthetic 12. A plurality of pressure cells $PC_n$ may be connected, via appropriate connecting means, such as manifolds, to the same or to separate cells in the prosthetic 12. Control unit 28 and microprocessor 29 may be preprogrammed or may respond to sensed physiological requirements and will typically be a hybrid; perhaps moderating a preprogrammed regime in accordance with the fluctuating requirements of the heart 14 as a result to the varying effort exerted by the patient throughout the day, and/or to modify the prosthetic 12 in accordance with the further deterioration of the heart 14 over time or perhaps the improvement as a result of possible therapeutic massaging effect of the present invention.

In one embodiment of the invention, the pressure of the outer chamber 184 of individual pressure cells PC is itself variable by pumping a low pressure fluid thereinto from an external reservoir 50 (see FIG. 1B), or therefrom into the external reservoir, by varying the size of the outer chamber 184, perhaps by a piston or bellows effect. Additionally, in some embodiments the residual fluid pressure within the high-density fluid may be varied by varying the effective quantity of saline within the loop by some appropriate means, such as pumping to and from a saline reservoir 23 for example.

Figure 8:
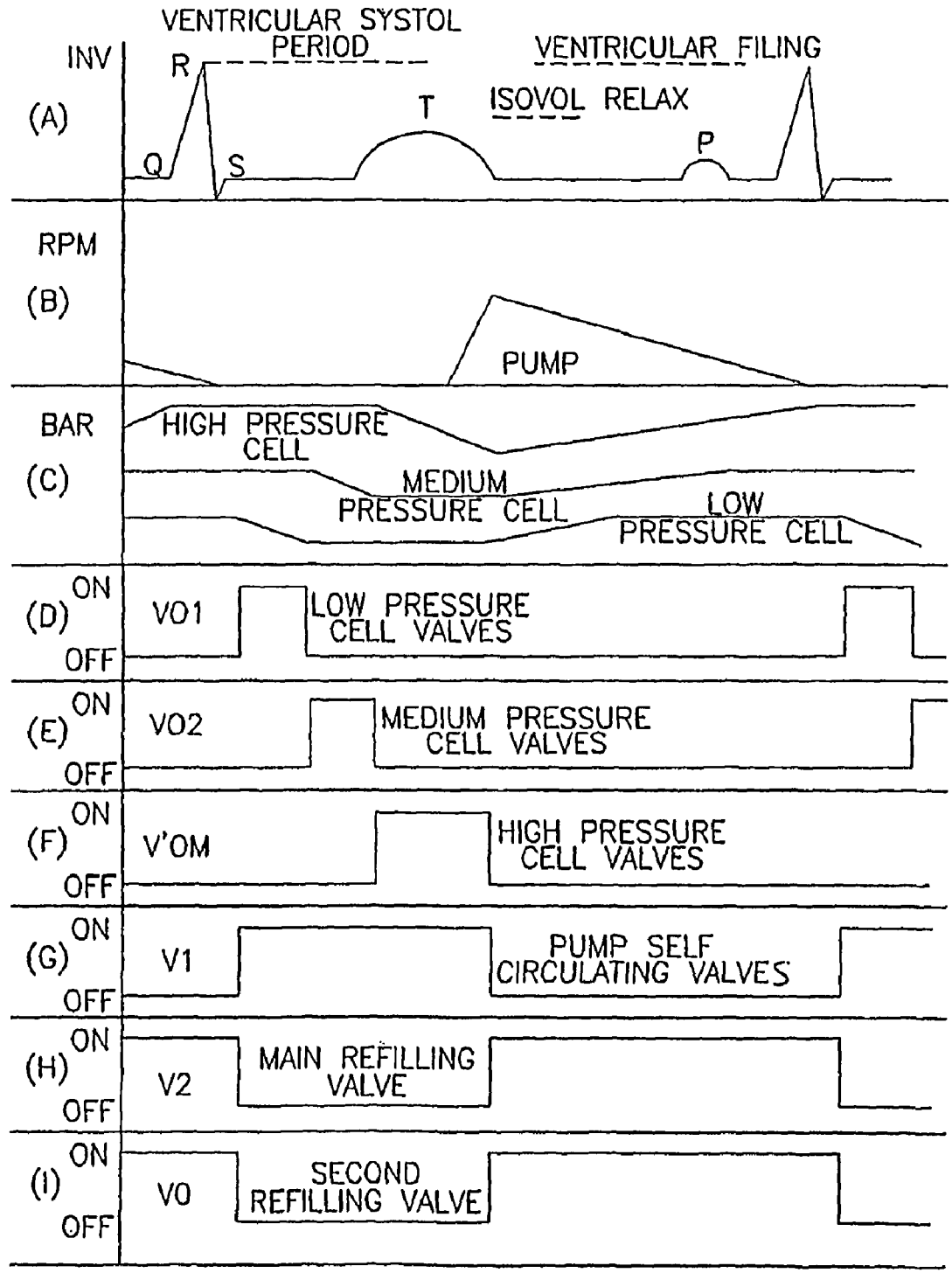
FIG. 8 is a timing diagram for the operation of the system exemplified in FIG. 1B, and includes the following graphs.

Referring now to the timing diagram of FIG. 8, the behavior of the embodiment of FIG. 1B is shown, over time, according to one algorithm for operation thereof, Graph (B) showing the pumping cycle of the pump 16, where shut-off valves $V_{o1}$ to $V_{om}$ are shown open and closed, Graphs (D)-(I); the effect on the pressure chambers of the prosthetic connected therewith is shown in Graph (C). This is matched to the heartbeat of a heart through the systolic and diastolic cycle seen in Graph (A) as monitored by the ECG 35. Clearly, a diseased heart will have mis-functioning atriums or ventricles, and the prosthetic will be configured to apply forces thereto, and each embodiment will be patient specific, nevertheless, the pressure-time Graph (C) does show how a gradual pulsation effect may be provided by a plurality of pressure cells PC, thereby allowing a shock free massaging effect suitable for long-term, or at least for bridging, and minimizing the likelihood of post-cardiotomy heart failure.

As explained hereinabove, each pressure cell PC may be configured to apply a pulse of a different magnitude. Thus three pressure cells, each capable of applying a different pressure P1, P2 and P3 can, where appropriate apply up to the full power set {P1, P2, P3}, that is $2^3$ or 8 different pressures, allowing the pressure to be built up in a controlled manner. Clearly, however, two or more pressure cells may apply pulses of substantially the same pressures. It will further be noted, that although the pressure cells apply discrete pressures, in practice, the pressure is built up smoothly and gradually due to hysteresis of the system 10.

The pulsating algorithm may be set, or may be controlled by the control unit 28 depending on the level of exertion, for example. Thus for assisting the heart of a patient in a relaxed state, such as asleep, perhaps only two cells will operate to provide two or three states, whereas whilst doing more work, perhaps whilst walking, more powerful pressure cells are provided, typically with more intermediate states to provide a gradual increase in assistance over the diastolic to systolic cycle. When patient performs more exerting exercise, such as whilst climbing stairs, all pressure cells may operate together to force the heart 14 to contract more effectively, thereby pumping more blood around the body. In preferred embodiments, the pumping algorithm used is dependent on signals provided by sensors monitoring vital statistics, such as an ECG monitoring sensor 35 on the heart 14 itself—perhaps with a blood pressure monitoring sensor (not shown).

Control of the valves V by the control unit 28 may be electronic, mechanical, pneumatic, or hydraulic.

The possibility of providing varying pressures to the different regions of the heart engaging prosthetic 12 in a controlled manner provides a means of ensuring that the prosthetic 12 stays in contact with the heart 14 during operation.

The system 10 disclosed herein has sufficient inherent flexibility to automatically adjust to changing heart characteristics, or to be adjusted by a cardiac specialist monitoring the health of the patient. Consequently, the solution described herein may be employed not merely as a temporary or bridging device for patients awaiting transplant, but also as a long term solution that adapts itself to changing physiological needs of patient and to deterioration of the heart 10. For example, a device is contemplated that is designed to provide a pumping effect to the left ventricle, with shut-off valves isolating compressive chambers or bladders around the right ventricle. If subsequent deterioration of the heart requires assistance to the right ventricle, the shut off valve may be opened, to allow a dilating pulse to be applied thereto. Furthermore by careful control, and ongoing monitoring by a cardiologist, the device can actually exercise the heart muscle and may provide a physiotherapeutic effect thereto.

The present invention thus provides advanced heart assist devices having hitherto unavailable degrees of freedom to provide a tailored solution to the requirements of specific patients.

It is a particular feature of preferred embodiments for cardiac assist applications, that the cardiac engaging prosthetic is a modular device constructed from a kit of elements that may be assembled to provide a tailor made, individual solution for a particular diseased heart, having characteristics perhaps only fully appreciated once the diseased heart is exposed during open-heart surgery. The cardiac engaging prosthetic may be cup shaped, frustoconical, cylindrical etc. and may be tailored to the shape of the individual heart to provide a tailored solution for a specific diseased heart. The cardiac engaging prosthetic may be coupled to the heart via any of the conventional techniques, including stitches for example. Preferably the cardiac engaging prosthetic is attached via silicone rings that encircle the heart and/or to the various arteries and veins. Since such silicone rings may be inelastic, it will be appreciated that in general; the expansion of the cells of the heart assist device will apply forces in three dimensions and, depending on design, may pull as well as push.

In case of failure, the system's valves are preferably configured to open or close to fail safe positions, so as to relax the prosthetic and free the heart from all constricting pressure.

It will be appreciated that the system described hereinabove may be modified and applied around a limb, such as in a tourniquet type prosthetic belt around the thigh of a diabetic patient, to pressure treat the limb and aid blood circulation therein.

The various components of the embodiments of the present invention may be fabricated from a wide variety of materials. For example, suitable types of polymeric materials for the various components of the present invention include polyester, poly-methyl methacrylate (PMMA), polyurethane, velour, silicone, Dacron, silastic, and Avcorone. Titanium and steel are other suitable materials. Clearly, combinations of different materials such as plastic coated titanium for example, may be used as and where appropriate.

Persons skilled in the art will appreciate that the present invention is not limited to what has been particularly shown and described hereinabove. Rather the scope of the present invention is defined by the appended claims and includes combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. An organ assist system comprising, in a closed system of recirculating fluid:
   a ring-shaped prosthetic that contactively surrounds at least a portion of a body part, including a plurality of bladders adapted for selectable dilation and contraction in response to a varying fluid pressure therewithin;
   a fluid pump in fluid communication with said prosthetic and in series connection therewith;
   at least one array comprised of a plurality of pressure cells;
   conduits connecting said bladders in said prosthetic, pump and plurality of pressure cells;
   a control unit of a control system for controlling operation of at least said fluid pump;

a plurality of pressure sensors within said closed hydraulic system, said pressure sensors in fluid communication with said prosthetic and operative to monitor fluid pressure in said system;

a power source in transcutaneous electrical communication with said control unit; and a plurality of shut off valves, one of said valves positioned in one of said conduits leading away from said prosthetic and leading to said pump and operative for closing said conduit, and a second said valve positioned in a bypass conduit and operative to enable said pump to be bypassed thereby, wherein each of said pressure cells comprises a cage of a substantially rigid biocompatible material divided into an inner chamber and an outer chamber by a flexible elastic wall, said outer chamber being a sealed chamber bounded by said cage and said flexible elastic wall and being filled with a low-density gas, and said inner chamber being defined by said flexible elastic wall, having an inlet and an outlet that are closable by fast action shut-off valves and being filled with a liquid, the maximum pressure of each pressure cell being defined by the pressure in said sealed outer chamber; and wherein one of said at least one arrays comprises of a plurality of pressure cells positioned upstream of said prosthetic, each pressure cell having controlled fast action shut-off valve at said inlet thereinto, and a second controlled fast action shut-off valve at said exit therefrom, said controlled fast action shut-off valves being controlled by said control unit of said control system such that said plurality of pressure cells may provide a range of pressurizations to said bladders of said prosthetic for applying a controlled variable pressurizing effect to the body part thereby.

2. The system of claim 1, wherein said plurality of pressure cells comprises a plurality of N pressure cells, and being capable of providing up to $2^N$ pulse intensities to bladders of said prosthetic.

3. The system of claim 2, wherein said plurality of pressure cells comprises an array of N pressure cells, operable in at least one of the following modes:
   a. parallel,
   b. series, and
   c. a combination of parallel and series.

4. The system of claim 1, wherein said at least one array comprised of a plurality of pressure cells is at least two arrays and wherein a second array is positioned downstream relative to said ring-shaped prosthetic.

5. The system of claim 1, wherein said flexible elastic wall is a tube of a flexible elastic material within said cage.

6. The system of claim 1, wherein desired pressurizations are obtainable from each said pressure cell with high accuracy by appropriate selection of volume of said sealed cage and control of pressure therein.

7. The system of claim 1, wherein said outer chambers of each of at least two of said plurality of pressure cells has a different size and/or a different internal pressure.

8. The system of claim 1, wherein outer chambers of each of said plurality of pressure cells are connected to a reservoir, such that minimum pressure within outer chamber, corresponding to a fully flattened inner chamber, is variable.

9. The system of claim 1, wherein said prosthetic comprises a plurality of components including conduits and bladders, selectable from a kit to provide a specific prosthetic adaptable to a specific body part of a specific patient.

10. The system of claim 1, wherein said prosthetic has a modular construction and comprises individual conduits, bladders and rigid backing plates, for arranging around the body part, in one or more layers thereby allowing tailoring of said prosthetic to a specific organ of a specific patient.

11. The system of claim 1, wherein said prosthetic is tailored to fit a specific organ of a specific patient by selecting and arranging appropriate sub-components to provide appropriate pressure characteristics locally where needed.

12. The system of claim 1, wherein the body part is a heart and said prosthetic is a heart engaging prosthetic that surrounds at least a part of said heart.

13. The system of claim 12, further comprising an ECG sensor coupled to said control unit to control said shut-off valves of said system in response to said pumping of the heart.

14. The system of claim 1, configured as a heart assist device for assisting a damaged heart to pump, wherein said plurality of pressure cells provides a diastolic pressure to prevent the relaxed heart from dilating.

15. The system of claim 1, configured as a heart assist device for assisting a damaged heart to pump, wherein said plurality of pressure cells provides a systolic pressure to assist the contraction of said heart and thus assist said pumping thereof.

16. The system of claim 1, wherein the body part is an internal organ and said control system is powered by a transcutaneous energy transmission (TET) system.

17. The system of claim 1, wherein said control unit is programmable prior to activation.

18. The system of claim 1, wherein said control unit is reprogrammable during operation.

19. The system of claim 1, wherein said control unit is responsive to changing needs.

20. The system of claim 1, wherein said fluid is saline.

21. A pressure cell for use within the system of claim 1, said pressure cell comprising a cage of a substantially rigid biocompatible material divided into an inner chamber and an outer chamber by a flexible elastic wall, said outer chamber being a sealed chamber bounded by said cage and said flexible elastic wall and being filled with a low-density gas, and said inner chamber being defined by said flexible elastic wall, having an inlet and an outlet that are closable by fast action shut-off valves and being filled with a liquid, the maximum pressure of said pressure cell being defined by the pressure in the sealed outer chamber.

22. The pressure cell of claim 21, wherein said flexible elastic wall is a tube of a flexible elastic material within said cage.

23. The pressure cell of claim 21, wherein said sealed cage has a volume predetermined to facilitate provision of a predetermined maximum pressure by said pressure cell.

24. The pressure cell of claim 21, wherein said outer chambers of said pressure cell are connected to a fluid reservoir, such that minimum pressure within outer chamber, corresponding to a fully flattened inner chamber, is variable.

25. The pressure cell of claim 21, wherein said minimum pressures within said cell and said pumping cycle thereof, is controllable by a programmable microprocessor.

26. The system of claim 1 further comprising a fluid reservoir and third and fourth shut-off valves, said valves provided to isolate from or to connect to the system said fluid reservoir via a conduit, said valves controlling the effective amount of recirculating liquid in the system and the ambient pressure therein.

27. A method of applying a controlled, variable pressure to a body part using the system of claim 1, by activating said fast action shut-off valves of said pressure cells of said pressurization apparatus in accordance with an algorithm.

* * * * *